United States Patent [19]

Tsai et al.

[11] Patent Number: 5,994,298
[45] Date of Patent: Nov. 30, 1999

[54] PROTEINS FOR CANCER CELL SPECIFIC INDUCTION OF APOPTOSIS AND METHOD FOR ISOLATION THEREOF

[76] Inventors: David Tsai; Jenny Yu, both of 2500 Townsgate Rd. Unit C, Westlake Village, Calif. 91361

[21] Appl. No.: 09/149,878

[22] Filed: Sep. 8, 1998

Related U.S. Application Data

[63] Continuation-in-part of application No. 08/993,432, Dec. 18, 1997.
[51] Int. Cl.$^6$ .............................. A61K 38/16; C07K 14/00
[52] U.S. Cl. ..................................... 514/8; 514/2; 514/21; 514/23; 514/908; 514/918; 514/920; 424/572; 530/350; 530/827; 530/828; 436/64
[58] Field of Search ..................................... 514/2, 8, 908, 514/918, 920, 21, 23; 424/572; 530/350, 827, 828; 436/64

[56] References Cited

U.S. PATENT DOCUMENTS

| 5,449,757 | 9/1995 | Serrero ..................................... 530/350 |
| 5,639,727 | 6/1997 | Little et al. ............................... 514/12 |

FOREIGN PATENT DOCUMENTS

97/31107   8/1997   WIPO .

OTHER PUBLICATIONS

Wang et al., Oncogene, vol. 15 pp. 143–157, Sep. 1997.
Yang, et al., "Human a$_2$–HS–glycoprotein/bovine fetuin homologue identification and development regulation of the gene", Biochemica et Biophysica Acta 1130 (1992) 149–156.
Yoshioka, et al., "The Complete Amino Acid Sequence of the A–chain of Human Plasma a$_2$HS–glycoprotein", The Journal of Biological Chemistry, vol. 261, No. 4, pp. 1665–1676 (1986).
Gejyo, et al., "Characterization of the B–Chain of Human Plasma a$_2$HS–Glycoprotein", The Journal of Biological Chemistry, vol. 258 No. 8, pp. 4966–4971 (1983).
von Bulow, et al., "Human fetuin/a$_2$HS glycoprotein in colloid and parenchymal cells in human fetal pituitary gland", Histochemistry, (1993) 99:13–22.
Spiro, "Studies on Fetuin, a glycoprotein of Fetal Serum" The Journal of Biological Chemistry, vol. 235, No. 10, pp. 2860–2869.
Grant, et al., "Effects of Epidermal Growth Factor, Fibroblast Growth Factor, and Transforming Growth Factor–B on Cornmeal Cell Chemotaxis", Ivestigative Ophthalmology & Visual Science, vol. 33, No. 12 (1992).

Wiley, et al., "Identification and Characterization of a New Member of the TNF Family That Induces Apoptosis", Immunity vol. 3, 673–682 (1995).
Kawakami, et al., "Cachectin/TNF Kills or Inhibits the Differentiation fo 3T3–L1 Cells According to Developmental Stage", J. of Cellular Physiology, 138:1–7 (1989).
Krammer. et al., "Apoptosis in the APO–1 System", Apoptosis: The Molecular basis of Cell Death, pp. 87–99 (1991).
Lin, et al., "Invitro Apoptosis in the Human Hepatoma Cell Line Induced by Transforming Growth FActor B$_1$", Cancer Research, 52, 385–388 (1992).
Grotendorst, et al., "Attachment of smoth muscle cells to collagen and their migration toward platelet–derived growth factor", Proc. Natl. Acad. Sci. USA, vol. 78, No. 6, pp. 3669–3672 (1991).

*Primary Examiner*—Bennett Celsa
*Attorney, Agent, or Firm*—Trojan Law Offices; R. Joseph Trojan; Katharine H. Kohies

[57] ABSTRACT

The present invention provides the methods to isolate the proteins specifically induced apoptosis (programmed cell death) in prostate cancer cells (LNCAP), leukemia cells (HL-60), and breast cancer cells (MCF-70), but without effect in normal human lung fibroblast cells (CCD 39 Lu). P-1 has no effect on breast cancer cells. Five proteins have been isolated from the conditioned media of culture cells: (1) Apogen P-1: the proteins (Apogen P-1a, Apogen P-1b and Apogen P-1c) isolated from the conditioned medium of XC cells are able to induce apoptosis in prostate cancer cells (LNCAP) without effect in normal human lung fibroblast (CCD 39 Lu), colon cancer (T84), breast cancer (MCF-7) and leukemia (HL-60) cells. (2) Apogen P-2: the protein isolated from the conditioned medium of C3H10T1/2 cells is able to induce apoptosis in prostate cancer cells (LNCAP) and breast cancer (MCF-7) without effect in normal human lung fibroblast (CCD 39 Lu) and colon cancer (T84) cells. (3) Apogen L: the protein isolated from the conditioned medium of XC cells is able to induce apoptosis in leukemia cells (HL-60), and breast cancer (MCF-7) without effect in normal human lung fibroblast (CCD 39 Lu), colon cancer (T84) and prostate cancer (LNCAP) cells. The isolated protein Apogen P-2 is at least in part comprised of bovine fetuin. When properly prepared, fetuin is able to induce apoptosis in leukemia cells (HL-60), prostate cancer (LNCaP and PC-3) cells, colon cancer (Colo 205) cells, breast cancer (MCF-7) cells, and lung cancer (Calu-1) cells. The invention may lead to the discovery of a novel class of anticancer drug that aims at prostate cancer, breast cancer, leukemia and other cancers by inducing apoptosis in cancer cells without affecting normal cells.

2 Claims, 23 Drawing Sheets

PROTEINS FOR CANCER CELL SPECIFIC INDUCTION OF APOPTOSIS AND METHOD FOR ISOLATION THEREOF

CLAIM OF PRIORITY

This application is a continuation-in-part to application Ser. No. 08/993432 filed Dec. 18, 1997.

BACKGROUND OF THE INVENTION

Human beings have had a long battle against cancer. Because the disease is so widespread, manifests itself in so many different ways and is so relentless, the potential market for effective cancer therapies is enormous. It is estimated that 10 million people in the U.S. either have or have had cancer. The National Cancer Institute (NCI) projects that in 1995, some 1.2 million new cases of cancer will be diagnosed in the United States, and that 538,000 people will die of the disease. Cancer is currently treated, with a low degree of success, with combinations of surgery, chemotherapy and radiation. The reason of the low degrees of success in cancer chemotherapy is as the following: Current chemotherapeutic approaches target rapidly dividing tumor cells. This approach is ineffective when the cancer is dormant or growing slowly. Such treatments also affect other, noncancerous cells that divide rapidly, causing harmful side effects.

Only in the last several years has a new approach emerged in the battle against cancer. This approach is based on the newly discovered biological phenomenon called "Apoptosis". Apoptosis is also called "programmed cell death" or "cell suicide". (Krammer, et al., "Apoptosis in the APO-1 System", Apoptosis: The molecular Basis of Cell Death, pp. 87–99 Cold Spring Harbor Laboratory Press, 1991). In contrast to the cell death caused by cell injury, apoptosis is an active process of gene-directed, cellular self-destruction and that it serves a biologically meaningful function. (Kerr, J. F. R and J. Searle J. Pathol. 107:41, 1971). One of the examples of the biologically meaningful functions of apoptosis is the morphogenesis of embryo. (Michaelson, J. Biol. Rev. 62:115, 1987). Just like the sculpturing of a sculpture, which needs the addition as well as removal of clay, the organ formation (Morphogenesis) of an embryo relies on cell growth (addition of clay) as well as cell death (removal of clay). As a matter of fact, apoptosis plays a key role in the human body from the early stages of embryonic development through to the inevitable decline associated with old age. (Wyllie, A. H. Int. Rev. Cytol. 68:251, 1980). The normal function of the immune, gastrointestinal and hematopoietic system relies on the normal function of apoptosis. When the normal function of apoptosis goes awry, the cause or the result can be one of a number of diseases, including: cancer, viral infections, auto-immune disease/allergies, neurodegeneration or cardiovascular diseases. Because of the versatility of apoptosis involved in human diseases, apoptosis is becoming a prominent buzzword in the pharmaceutical research field. Huge amounts of time and money are being spent in an attempt to understand how it works, how it can be encouraged or Inhibited and what this means for practical medicine. A handful of companies have been formed with the prime direction of turning work in this nascent field into marketable pharmaceutical products. The emergence of a core of innovative young companies combined with the tentative steps being taken by established industrial players are certain to make apoptosis research one of the fastest-growing and most promising areas of medical study of the 1990s.

The idea that cancer may be caused by insufficient apoptosis merged only recently (Cope, F. O and Wille, J. j, "Apoptosis": The Molecular Basis of Cell Death, Cold Spring Harbor Laboratory Press, p. 61, 1991). This idea however, opens a door for a new concept in cancer therapy—Cancer cells may be killed by encouraging apoptosis. Apoptosis modulation, based on the processes present in normal development, is a potential mechanism for controlling the growth of tumor cells. Restoring apoptosis in tumor cells is an attractive approach because, at least in theory, it would teach the cells to commit suicide. Nevertheless, since the objective of cancer treatment is to kill cancer cells without killing the host, although apoptosis may open a new door for cancer therapy by inducing apoptosis in tumor cells, the success of this treatment is still dependent on the availability of drugs that can selectively induce apoptosis in tumor cells without affecting normal cells. In this patent application, we described the methods for the Isolation of proteins that specifically induce apoptosis in cancer cells without effect in normal cells. These proteins may present a new class of anticancer drugs that induce apoptosis in cancer cells which may offer a breakthrough in cancer therapy.

DETAILED DESCRIPTION OF THE INVENTION

This patent application describes the isolation of five proteins named: Apogen P-1a, Apogen 1b, Apogen 1c, Apogen P-2 and Apogen L.

(A) Isolation of Apogen P-1

(1) Source of Apogen P-1

Apogen P-1 was isolated from the conditioned medium of a cell line called XC which was derived from rat tumor (ATCC CCL 165). XC cells were first grown in Dulbecco's Modification of Eagle's Medium (DMEM) containing 10% Fetal bovine serum (FBS) for 3 days. XC cells were then washed with PBS (3×100 ml) to remove serum and then grown in DMEM containing no FBS for 4 days. From this serum free conditioned medium, we detected an activity inducing apoptosis in a prostate cancer cell line called LNCAP. On the other hand, normal human lung fibroblast cell line (CCD 39 Lu) and breast cancer cells (MCF-7) is not affected by this activity.

(2) Activity of Apogen P-1

(a) Apoptosis Inducing Activity

The activity of the crude conditioned medium of XC cells was tested on the following cell lines: JEG-3 (Choriocarcinoma), G401 (Wilm's tumor) LNCAP (Prostate cancer), T84 (colon cancer), HL-60 (leukemia), breast cancer cells (MCF-7), and CCD 39 Lu (normal lung fibroblast). When 10 folds concentrated conditioned medium was incubated for 18 hours with the above cell lines in the presence of 5% serum, the conditioned medium induced apoptosis in JEG-3 cells (35%), G 401 cell (27%), LNCaP (100%) and without activity in CCD 39 Lu (0%), T84 (0%), MCF-7 (0%) and HL-60 (0%).

Apoptosis is a distinct type of cell death that differs fundamentally from degenerative death or necrosis in its nature and biological significance. A cell undergoing apoptosis is distinct from a cell undergoing necrosis both morphologically and biochemically. Morphologically, the earliest definitive changes in apoptosis that have been detected with the electron microscope are compaction of the nuclear chromatin into sharply circumscribed, uniformly dense masses about the nuclear envelop and condensation of the cytoplasms. Phase-contrast microscope of cells under apoptosis shows the condensation and the fragmentation of DNA and the budding of cell to form apoptotic body.

To morphologically demonstrated that the XC conditioned medium contains activity inducing apoptosis, LNCAP cells were incubated with control medium or the conditioned medium treated as described as above for 15 hr and then stained with Hoechst dye for 2 hours. As shown in FIG. 1A, the nuclei of the LNCAP cells that have been incubated with control medium are normal and healthy(A). However, the nuclei of the LNCAP cells that have been incubated with the conditioned medium (X20, exchanged to RPMI) shown the characteristic of apoptosis (FIG. 1(B)). First, the conditioned medium causes the condensation of nucleus, demonstrated by the more intense fluorescence light compared with the control nucleus in FIG. 1(A). Secondly, the nucleus condensation is accompanied by the fragmentation of DNA, demonstrated by the breakage of nucleus as shown in FIG. 1(B). As we have mentioned above, the nucleus condensation and DNA fragmentation are the morphological characteristic of cells under apoptosis. These results suggest that the conditioned medium from XC cells contains an activity inducing apoptosis in LNCAP cells. On the other hand, the conditioned medium fails to induce apoptosis in normal human lung fibroblast (CCD 39 Lu cells) and breast cancer cells (MCF-7). As shown in FIG. 2, the nuclei of CCD 39 Lu cells remain the same with or without incubating with the conditioned medium of XC cells (FIG. 2(A) and FIG. 2(B)).

(b) Cell Repelling Activity

The partially purified Apogen P-1b (Q2 anionic exchanger chromatography step) isolated as described below was recently found to contain an activity other than inducing apoptosis. We found that Apogen P-1b have the activity to repel cells away. This activity is opposite to that of growth factors; many growth factors such as Platelet Derived Growth Factor (PDGF), Epidermal Growth factor (EGF), Fibroblast Growth factor (FGF) or Transforming Growth factor (TGF) function as a "chemoattractant"—which means that these growth factors attract cells toward them. (Grotendorst, G. R. et al., Proc. Natl. Acad. Sci. 78:3669, 1981; Grant, M. B. et al Invest. Ophthal. Visual Science. 33:3292, 1992). This finding suggests that Apogen P-1b isolated in this invention plays opposite biological functions as that of growth factors. For example, growth factors induce cell growth and attract cells, whereas Apogen P-1b induces cell death and repel cells. Apogen P-1b is the first "chemorepellent" found in the field of modern biology.

A tissue culture device called Transwell Insert purchased from Costar (Cambridge, Mass.) was used to discover the chemorepellent activity of Apogen P-1b. This device, which has been widely used for the studies of cell migration/invasion, contains an upper chamber and a lower chamber. Between these two chambers is a polyester microporous membrane with 3.0 um pore size which allows cell to migrate through the membrane. Tested cells are grown on the upper chamber and tested compound is placed in the lower chamber. If this tested compound is a chemoattractant, we should see more cells migrate through the membrane than the control sample. In our experiments, Hep G2 (100,000 cells) cells, which have cell size 3–4 times as big as the membrane pore size were grown in the upper chamber for 2 hours and then the partially purified Apogen-1b (30 $\mu$l) isolated by ammonium sulfate precipitation and Q2 HPLC chromatography as described above was placed in the lower chamber. After 15 hours, cells that have migrated through the membrane were collected by treating the membrane with 0.2 ml of trypsin solution for 30 min. Cells in ten microliters of the trypsin solution were counted in a Hemacytometer. In several experiments, we found that the partially purified Apogen-1b contained an activity decreasing the number of cells going through the membrane. For example, in one experiment, in the presence of the partially purified Apogen P-1b, the cells number in 10 microliters trypsin solution (which are the cells go through membrane) is 24+−4, whereas the cells number that go through membrane in the control experiment is 82+−27. This result suggests that the partially purified Apogen P-1b prevents Hep G2 cells migrating through membrane. To unequivocally shown that Apogen P-1b repel cells, an inverted experiment was installed, instead of placing Apogen P-1b in the lower chamber, we placed Apogen P-1b in the upper chamber, after 12 hours, we found that 56+−19 cells went through membrane compared with control experiment of 30+−1.7 cells per 10 microliters of trypsin solution. The statistically significant increase or decrease in cell number going through the membrane by alternatively placing Apogen P-1b in the upper or lower chamber of this tissue culture device strongly suggests that Apogen P-1b repels cells.

(3) Isolation of Apogen P-1 from XC Conditioned Medium

The Apogen P-1 present in the conditioned medium was isolated by the following steps:

Step 1: Ammonium Sulfate Precipitation

Apogen P-1 was precipitated by 80% saturated of ammonium sulfate by adding 561 g of ammonium sulfate per liter of conditioned medium. Pellet was collected by centrifugation and the proteins were dissolved in 10 mM Tris-HCl (pH 7.4). After removal of ammonium sulfate by dialysis, the dissolved proteins were separated by a Q2 HPLC column.

Step 2: Q2 HPLC Chromatography

The dissolved proteins isolated by ammonium sulfate precipitation were concentrated and loaded on to a Q2 column (Bio-Rad) which is further developed by a linear gradient constructed by buffer A (10 mM Tris-HCl, pH 7.4) and buffer B (10 mM Tris-HCl, pH 7.4. 0.55 M NaCl) using BioRad's BioLogic HPLC system. The linear gradient was constructed by increasing buffer B from 0% to 100% in buffer A within 10 min (20 milliliter elution volume and thereafter the column was eluted with 100% buffer B for 5 min. The chromatogram is shown in FIG. 3.

The Apogen P-1 activity was assayed by the induction of apoptosis in LNCAP cells. We found that there are three activity peaks across the chromatogram profile. Fraction 5 to 7 cause 70% cell death, fraction 8–10 cause 65% cell death and fraction 11–14 caused 90% cell death in 18 Hr. We collected fractions 5–7 and named it Apogen P-1a, fractions 8–10 is named Apogen P-1b and fractions 11 to 14 is named Apogen P-1c. These three Apogen P-1's were further purified by a reverse phase column.

Step 3: Reverse Phase Chromatography

Apogen P-1a, Apogen P-1b and Apogen P-1c were separately concentrated to 1.5 ml. One ml of methanol containing 0.05% trifluoracetic acid was added. In each samples, large amount of proteins were precipitated by this treatment. Whereas, the apoptosis inducing activity remained in supernatant. The supernatant was then applied to a reverse phase RP4 column (Micra Scientific Inc) and developed by a linear gradient constructed by solution A ($H_2O$, 0.05% TFA) and solution B (Methanol, 0.05% TFA). The linear gradient was constructed by increasing solution B from 0% to 100% in solution A within 10 min (20 milliliter elution volume and thereafter the column was eluted with 100% solution B for 5 min.)

Step 4: Preparative Electrophoresis

Apogen 1c isolated by anion exchange chromatography was purified by both Reverse phase chromatography (step 3)

and Preparative Electrophoresis by a MiniPrep Gel electrophoresis (Bio-Rad) The reverse phase chromatogram of Apogen P-1a is shown in FIG. 4(a) fractions 12–13 have activity inducing 80% cell death in LNCAP cells at 10 hr. The reverse phase chromatogram of Apogen P-1b is shown in FIG. 4(b). fractions 14 and 15 have activity inducing 45% cell death in LNCAP cells at 18 hr.

The reverse phase chromatogram of Apogen P-1c is shown in FIG. 4(c). fraction No 5 have activity inducing 52% cell death in LNCAP cells at 18 hr.

The purity of the isolated Apogen P-1a, Apogen P-1b and Apogen P-1c were checked with SDS-polyacrylamide gel electrophoresis stained with silver staining.

(1) Apogen P-1a: As shown in FIG. 5, a protein band with molecular weight of 70 KD was obtained. This result suggest the nearly successful purification of Apogen P-1a which have molecular weight of 70 KD on SDSPAGE.

(2) Apogen P-1b: A single faint protein band with molecular weight of 55 KD was obtained. This result suggest the successful purification of Apogen P-1b which have molecular weight of 55 KD on SDS-PAGE. (Data not shown)

(3) Apogen P-1c: The purification of Apogen 1c by Reverse Phase chromatography leads to the isolation of a 70 KD protein whereas the purification of Apogen-1c by preparative electrophoresis leads to the purification of a 57 KD protein. As shown in FIG. 6(A), a major protein band with molecular weight of 70 KD was obtained by Reverse Phase chromatography. A 57 KD protein, on the other hand, was isolated by preparative electrophoresis. (FIG. 6B).

Our next step, obviously, will be put our entire efforts on obtaining enough protein band for amino acid sequence.

(B) Isolation of Apogen P-2

(1) Source of Apogen P-2

Apogen P-2 was isolated from the conditioned medium of a cell line called C3H 10T1/2 which was derived from mouse embryo cells (ATCC CCL 226). C3H 10T1/2 cells were first grown in alpha Modification of Eagle's Medium (alpha-MEM) containing 10% Fetal bovine serum (FBS) for 3 days. Cells were then washed with PBS (3×100 ml) to remove serum and then grown in alpha-MEM containing no FBS for 4 days. From this serum free conditioned medium, we detected an activity inducing apoptosis in a prostate cancer cell line called LNCAP. On the other hand, normal human lung fibroblast cell line (CCD 39 Lu) is not affected by this activity.

(2) Activity of Apogen P-2

(a) Apoptosis Inducing Activity

The activity of the crude conditioned medium of C3H 10T1/2 cells was tested on the following cell lines: LNCAP (Prostate cancer), breast cancer cells (MCF-7), and CCD 39 Lu (normal lung fibroblast). When 10 folds concentrated conditioned medium was incubated for 18 hours with the above cell lines in the presence of 5% serum, the conditioned medium induced apoptosis in LNCaP (100%) and without activity in CCD 39 Lu (0%). To morphologically demonstrated that the C3H 10T1/2 conditioned medium contains activity inducing apoptosis, LNCAP cells were incubated with control medium or the conditioned medium treated as described as above for 15 hr and then stained with Hoechst dye for 2 hours. As shown in FIG. 7A, the nuclei of the LNCAP cells that have been incubated with control medium are normal and healthy(A). However, the nuclei of the LNCAP cells that have been incubated with the conditioned medium shown the characteristic of apoptosis (FIG. 7B). First, the conditioned medium causes the condensation of nucleus, demonstrated by the more intense fluorescent light compared with the control nucleus in FIG. 7A. Secondly, the nucleus condensation is accompanied by the fragmentation of DNA, demonstrated by the breakage of nucleus as shown in FIG. 7B. As we have mentioned above, the nucleus condensation and DNA fragmentation are the morphological characteristic of cells under apoptosis. The same held true of breast cancer cells (MCF-7) in which 85% apoptotic effect was observed after 18 hours of exposure to P-2. These results suggest that the conditioned medium from C3H10T1/2 cells contains an activity inducing apoptosis in LNCAP and MCF-7 cells. On the other hand, the conditioned medium fails to induce apoptosis in normal human lung fibroblast (CCD 39 Lu cells). As shown in FIG. 8, the nuclei of CCD 39 Lu cells remain the same with or without incubating with the conditioned medium of C3H10T1/2 cells (FIG. 8A and FIG. 8B).

(b) Cell Repelling Activity

The partially purified Apogen P-2 isolated by ammonium sulfate precipitation, hydroxylapatite and heparin treatment as described above was recently found to contain an activity other than inducing apoptosis. Similar to Apogen P-1b, Apogen P-2 have the activity to repel cells away. Transwell Insert purchased from Costar (Cambridge, Mass.) was used to discover the chemorepellent activity of Apogen P-2. This device, which has been widely used for the studies of cell migration/invasion, contains an upper chamber and a lower chamber. Between these two chambers is a polyester microporous membrane with 3.0 $\mu$m pore size which allows cell to migrate through the membrane. Tested cells (HL-60) were grown on the upper chamber and tested compound (Apogen P-2) is placed in the lower chamber. In our experiments, HL-60 (100,000 cells) cells, which have cell size 2–3 times as big as the membrane pore size were grown in the upper chamber for 2 hours and then the partially purified Apogen P-2 (30 $\mu$l) isolated by ammonium sulfate precipitation, hydroxylapatite and Heparin agarose as described above was placed in the lower chamber. After 6 hours, cells that have migrated through the membrane were collected from the lower chamber, the medium in lower chamber (0.6 ml) was centrifuged for 10 min and the HL-60 cells that went through the membrane were collected and resuspended in 80 $\mu$l of PBS. Cells in ten microliters of the PBS solution were counted in a Hemacytometer. In several experiments, we found that the partially purified Apogen P-2 contained an activity decreasing the number of cells going through the membrane. For example, in one experiment, in the presence of the partially purified Apogen P-2, the cells number in 10 microliters PBS solution (which are the cells go through membrane) is 47+−5.6, whereas the cells number that go through membrane in the control experiment is 213+−40. At this moment, no apoptosis was observed in HL-60 cells present in the upper chamber. This result suggests that the partially purified Apogen P-2 prevents HL-60 cells migrating through membrane.

(3) Isolation of Apogen P-2 from C3H10T1/2 Conditioned Medium

The Apogen P-2 present in the conditioned medium was isolated by the following steps:

Step 1: Ammonium Sulfate Precipitation

Apogen P-2 was precipitated by 80% saturated of ammonium sulfate by adding 561 g of ammonium sulfate per liter of conditioned medium. Pellet was collected by centrifugation and the proteins were dissolved in 10 mM Tris-HCI (pH 7.4).

Step 2: Hydroxylapatite Treatment

After removal of ammonium sulfate by dialysis in 10 mM Tris-HCI (pH 7.5), the dissolved proteins were incubated with Hydroxylapatite gel (Bio-Gel HTP gel, Bio-Rad) for 1 Hr. After remove HTP gel by centrifugation, the activity inducing apoptosis in LNCAP cells was found to present in the supernatant which was then further treated with Heparin agarose gel.

Step 3: Heparin Agarose Treatment

The supernatant from step 2 was further incubated with Heparin agarose (Sigma) for 1 Hr. After remove HTP gel by centrifugation, the activity inducing apoptosis in LNCAP cells was found to be present in the supernatant.

Step 4: Reverse Phase Chromatography

Apogen P-2 presents in the supernatant of Heparin agarose in step 3 was further purified by a reverse phase chromatography. Apogen P-2 was concentrated to 1 ml. One milliliter of methanol containing 0.05% Trifluoracetic acid was added. Large amount of proteins were precipitated by this treatment. Whereas, the apoptosis inducing activity (P-2) remained in supernatant. The supernatant was then applied to a reverse phase RP-4 column (Micra Scientific Inc) and developed by a linear gradient constructed by solution A ($H_2O$, 0.05% TFA) and solution B (Methanol, 0.05% TFA). The linear gradient was constructed by increasing solution B from 0% to 100% in solution A in 10 min (20 milliliter elution volume and thereafter the column was eluted with 100% solution B for 5 min.

The reverse phase chromatogram of Apogen P-2 is shown in FIG. 9. Fractions 12–14 have activity inducing 80% cell death in LNCAP cells at 12 hr. The purity of the isolated Apogen P-2 was checked with SDS polyacrylamide gel electrophoresis stained with silver staining. A single protein band with molecular weight of 65 Kd was obtained (FIG. 10)

(C) Isolation of Apogen L (1) Source of Apozen L

Apogen L was isolated from the conditioned medium of XC cell line (ATCC CCL 165). XC cells were grown in Dulbecco's Modification of Eagle's Medium (DMEM) containing 10% Fetal bovine serum (FBS) for 4 days. From this conditioned medium, we detected an activity inducing apoptosis in a leukemia cell line called HL-60. On the other hand, normal human lung fibroblast cell line (CCD 39 Lu) is not affected by this activity.

(2) Isolation of Apozen L from XC Conditioned Medium

The Apogen L present in the conditioned medium was isolated by the following steps:

Step 1: DE52 Absorption

The conditioned medium was incubated with the anion exchanger, DE 52 (Diethylaminoethyl cellulose, Whatman) for 1 hr. The incubation mixture was centrifuged and DE 52 which binds Apogen L was collected and washed with 10 mM Tris-HCI (pH 7.5) containing 0.15 M NaCl. Apogen L was then eluted from DE 52 cellulose by 10 mM Tris-HCI (pH 7.5) containing 0.5 M NaCI.

Step 2: Heparin Agarose Absorption

Apogen L isolated as described in step 1 was further absorbed by Heparin agarose (Sigma) by incubating Apogen L with Heparin agarose for 1 hr. Heparin agarose was collected by centrifugation and was washed with 10 mM Tris-HCI (pH 7.5). Apogen L absorbed in Heparin agarose was then eluted by 2 M NaCI.

Step 3: Q2 HPLC Chromatography

Apogen L isolated as described above was concentrated and loaded onto a Q2 column (Bio Rad) which is further developed by a linear gradient constructed by buffer A (10 mM Tris-HCI, pH 7.4) and buffer B (10 mM Tris-HCI, pH 7.4. 0.5 M NACI) using Bio-Rad's BioLogic HPLC system. The linear gradient was constructed by increasing buffer B from 00/o to 100% in buffer A within 10 min. The chromatogram is shown in FIG. 12. The purity of the isolated Apogen L was checked with SDS polyacrylamide gel electrophoresis stained with silver staining. A single protein band with molecular weight of 55 Kd was obtained (FIG. 11)

(3) Activity of Apogen L

The activity of Apogen L isolated as described above was tested on the following cell lines: HL-60 (leukemia) and CCD 39 Lu (normal lung fibroblast). To morphologically demonstrated that Apogen L contains activity inducing apoptosis, HL-60 cells were incubated with Apogen L isolated as described as above for 15 hr and then stained with Hoechst dye for 2 hours. As shown in FIG. 13A, the nuclei of the HL-60 cells that have been incubated with control medium are normal and healthy (FIG. 13A). However, the nuclei of the HL-60 cells that have been incubated with Apogen L shown the characteristic of apoptosis (FIG. 13B). First, Apogen L causes the condensation of nucleus, demonstrated by the more intense fluorescent light compared with the control nucleus in FIG. 13A. Secondly, the nucleus condensation is accompanied by the fragmentation of DNA, demonstrated by the breakage of nucleus as shown in FIG. 13B. As we have mentioned above, the nucleus condensation and DNA fragmentation are the two morphological characteristic of cells under apoptosis. These results suggest that the isolated Apogen L contains an activity inducing apoptosis in HL-60 cells. Apogen L also induces apoptosis in MCF-7 (breast cancer) cells. On the other hand, the conditioned medium fails to induce apoptosis in normal human lung fibroblast (CCD 39 Lu cells).

Figure 4A:
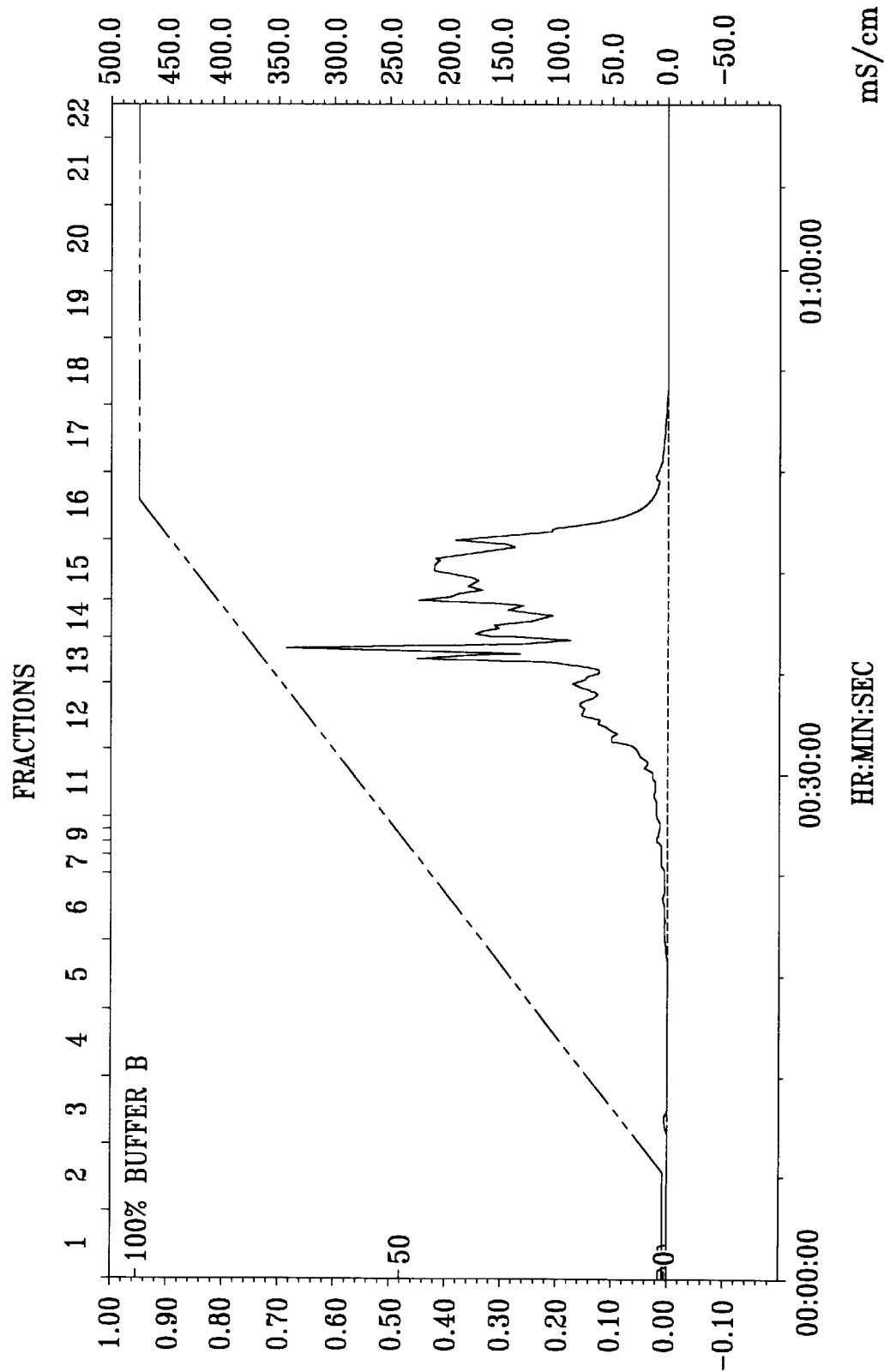
FIG. 4: Isolation of Apogen P-1 by Reverse Phase chromatography. Apogen P-1a, Apogen P-1b and Apogen P-1c were separately concentrated to 1.5 ml. One milliliter of methanol containing 0.05% Trifluoracetic acid was added. In each samples, large amount of proteins were precipitated by this treatment. Whereas, the apoptosis inducing activity remained in supernatant. The supernatant was then applied to a reverse phase RP-4 column (Micra Scientific Inc) and developed by a linear gradient constructed by solution A ($H_2O$, 0.05% TFA) and solution B (Methanol, 0.05% TFA). The linear gradient was constructed by increasing solution B from 0% to 100% in solution A within 10 min (20 milliliter elution volume and thereafter the column was eluted with 100% solution B for 5 min.

The reverse phase chromatogram of Apogen P-1a is shown in FIG. 4(a). fractions 12–13 have activity inducing 80% cell death in LNCAP cells at 10 hr.

Figure 4B:
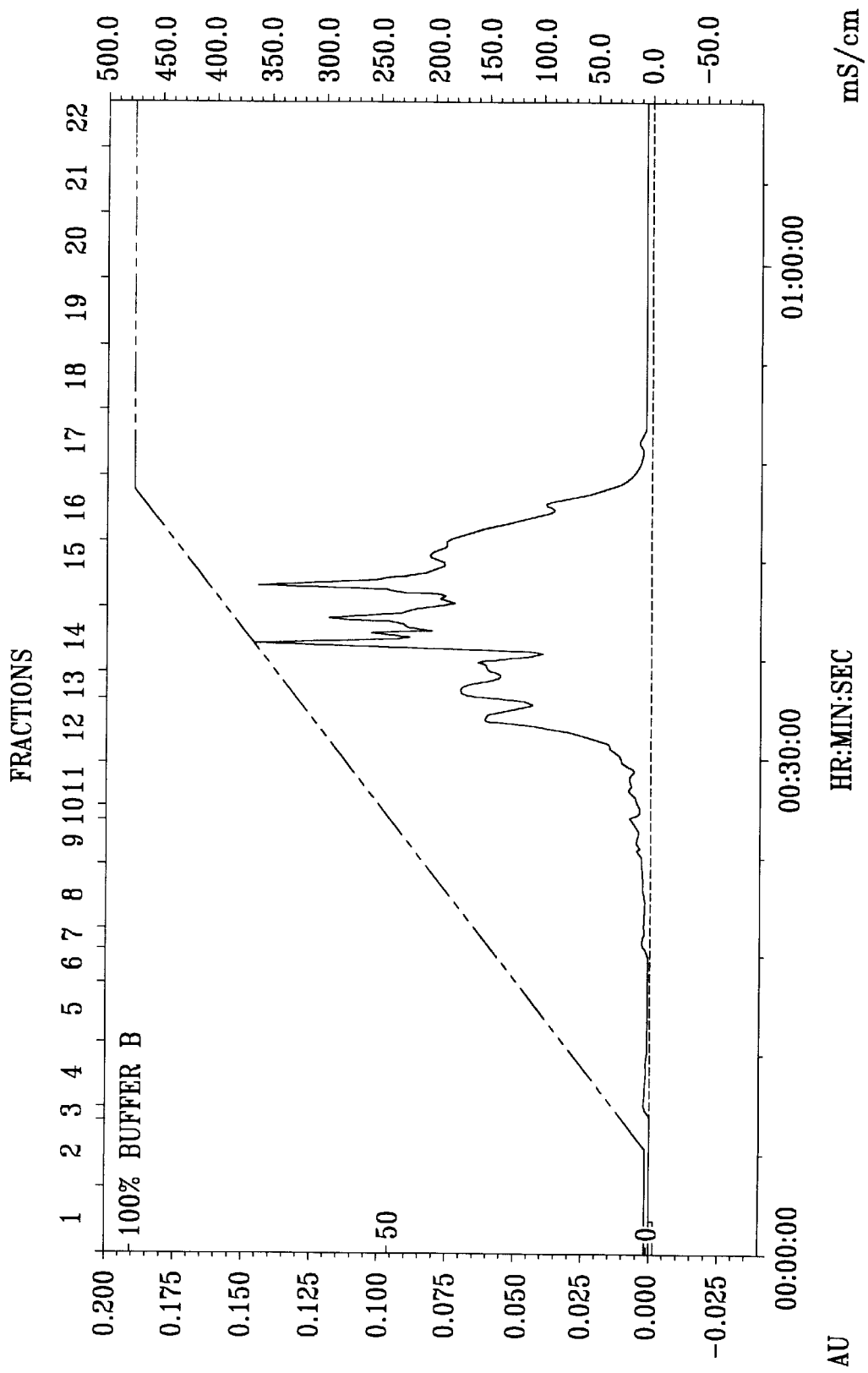

The reverse phase chromatogram of Apogen P-1b is shown in FIG. 4(b). fractions 14–15 have activity inducing 45% cell death in LNCAP cells at 18 hr.

Figure 4C:
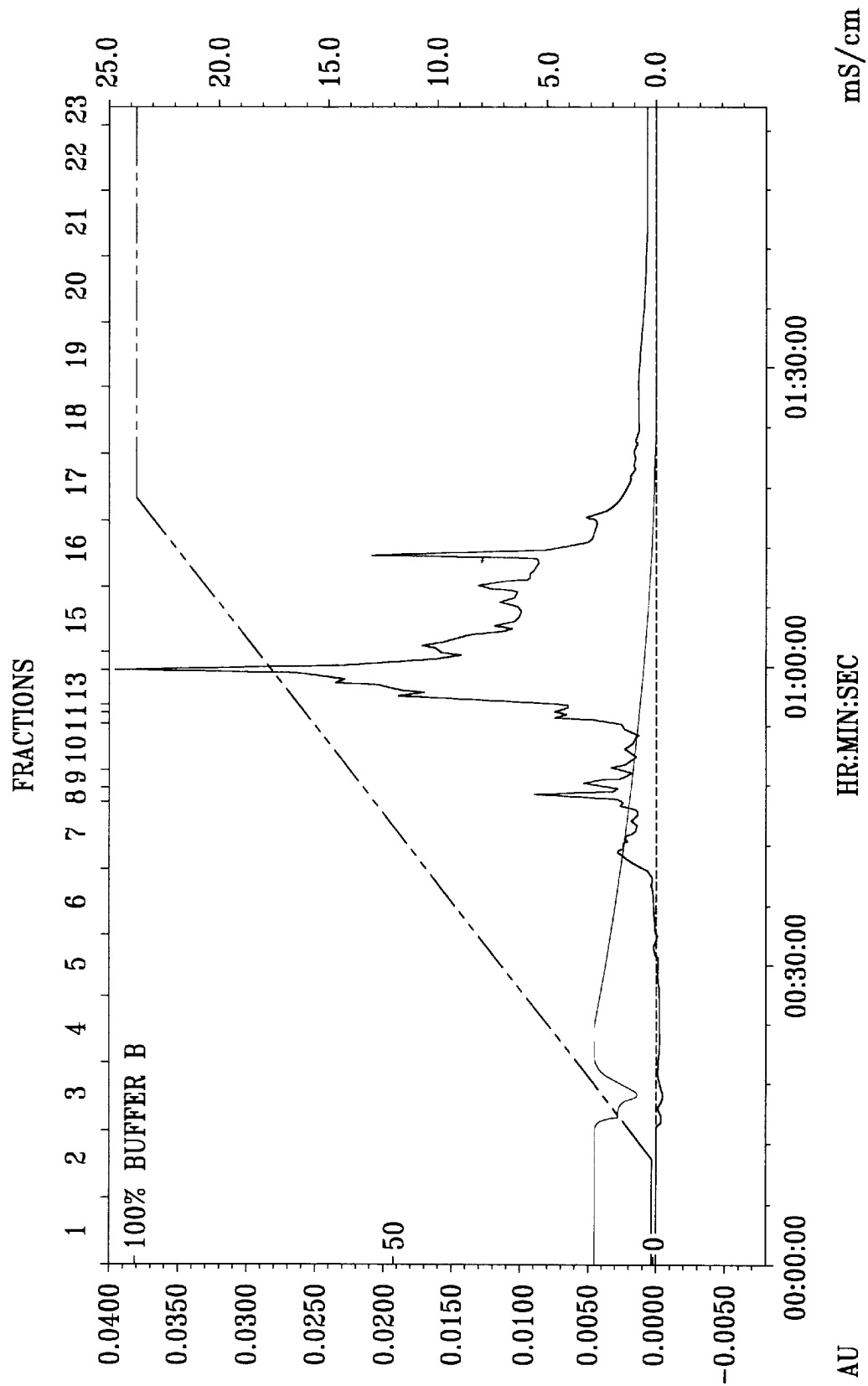

The reverse phase chromatogram of Apogen P-1c is shown in FIG. 4(c). fraction No. 5 have activity inducing 52% cell death in LNCAP cells at 18 hr.

The purity of the isolated Apogen P-1a, Apogen P-1b and Apogen P-1c were checked with SDS-polyacrylamide gel electrophoresis and stained with silver staining.

Figure 5:
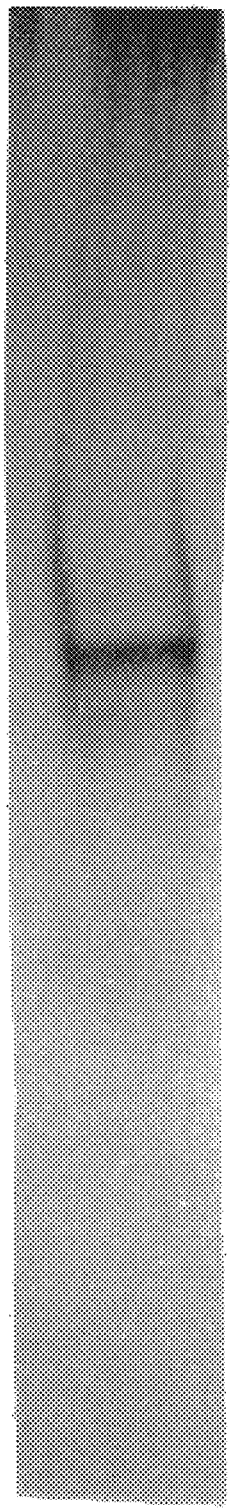

FIG. 5. Apogen 1a isolated by anion exchange chromatography and reverse phase chromatography was concentrated and subjected to electrophoresis under denaturing conditions through a 4–20% gradient Tris-Gly SDS-Polyacrylamide gel. The gel was silver stained. A major protein band with molecular weight of 70 KD was obtained. This result suggest the nearly successful purification of Apogen p-1c which have molecular weight of 70 KD on SDS-PAGE.

Figure 6A:
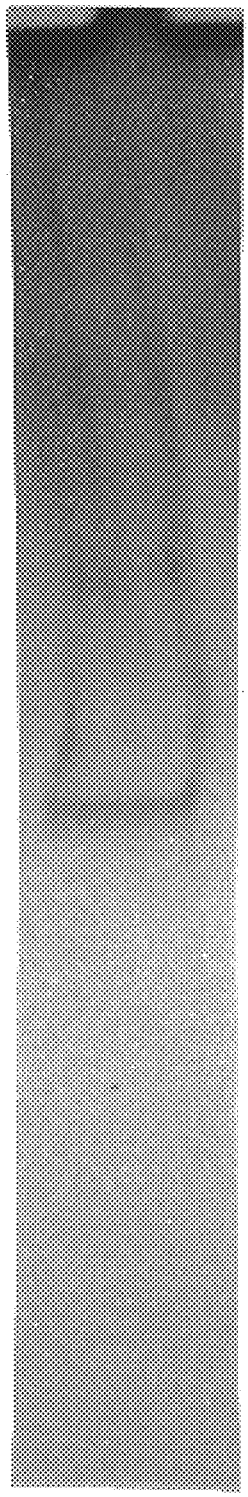
Figure 6B:
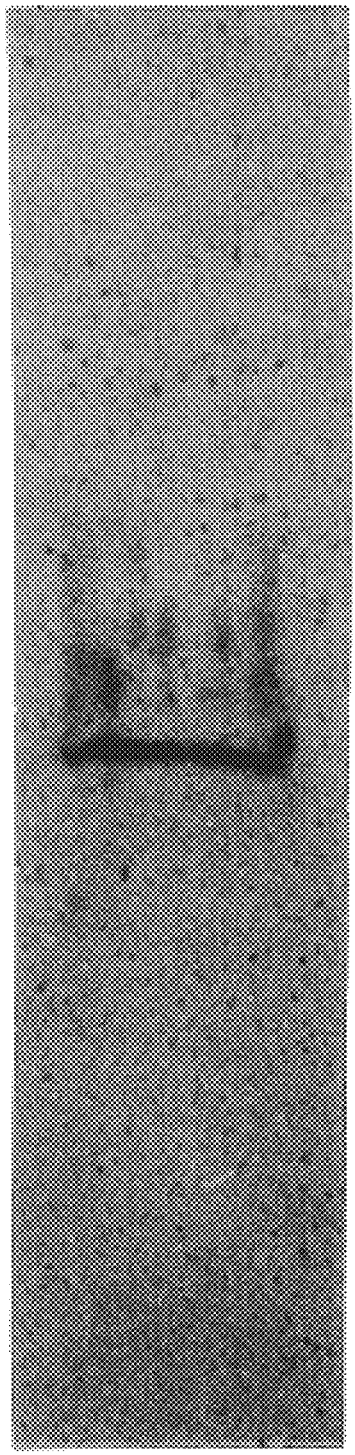

FIG. 6. Apogen 1c isolated by anion exchange chromatography and reverse phase chromatography and preparative electrophoresis were concentrated and subjected to electrophoresis under non-denaturing conditions through a 10% resolving gel and 4% stacking gel on SDS Polyacrylamide electrophoresis. The gel was silver stained. A protein band with molecular weight of 70 KD was obtained (FIG. 6A) This result suggest the successful purification of Apogen p-1c by reverse phase chromatography which have molecular weight of 70 KD on SDS-PAGE. The purification of Apogen 1c by preparative electrophoresis leads to the isolation of a protein with molecular weight of 57 KD (FIG. 6B). The possibility that these two proteins are the same protein with different fragment length is not able to rule out at this moment.

Figure 7A:
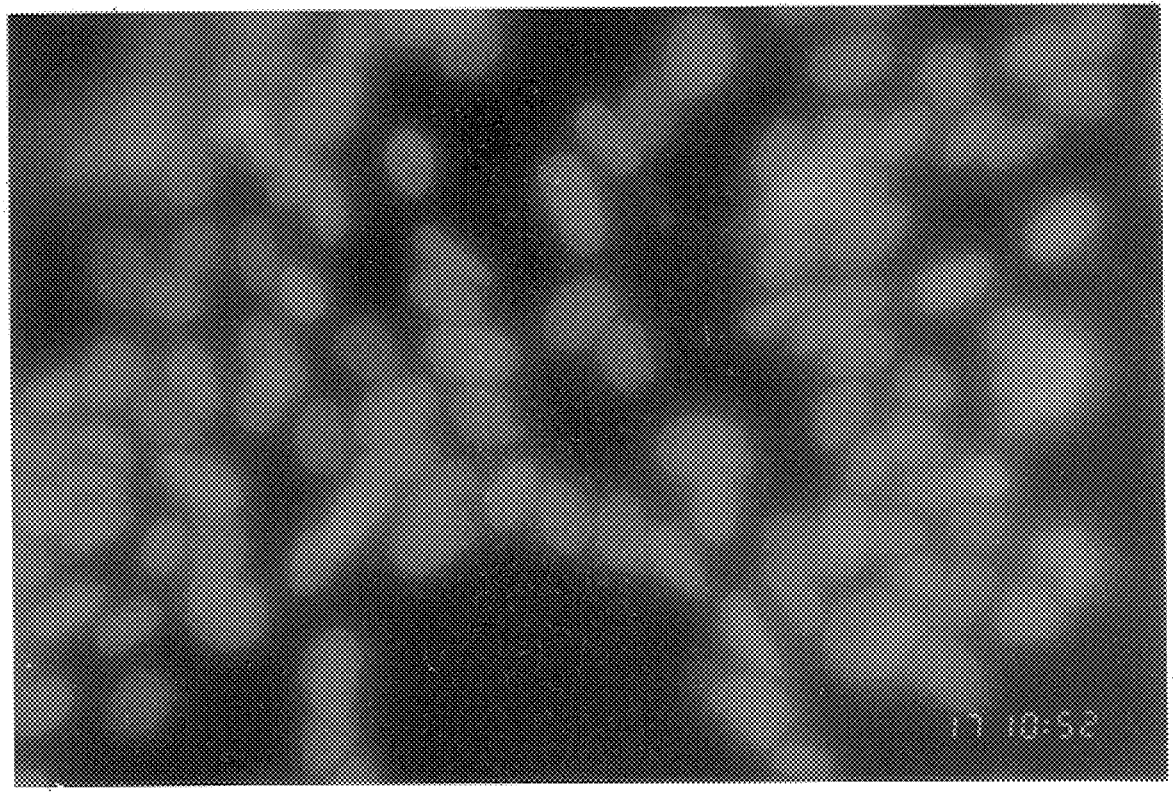
Figure 7B:
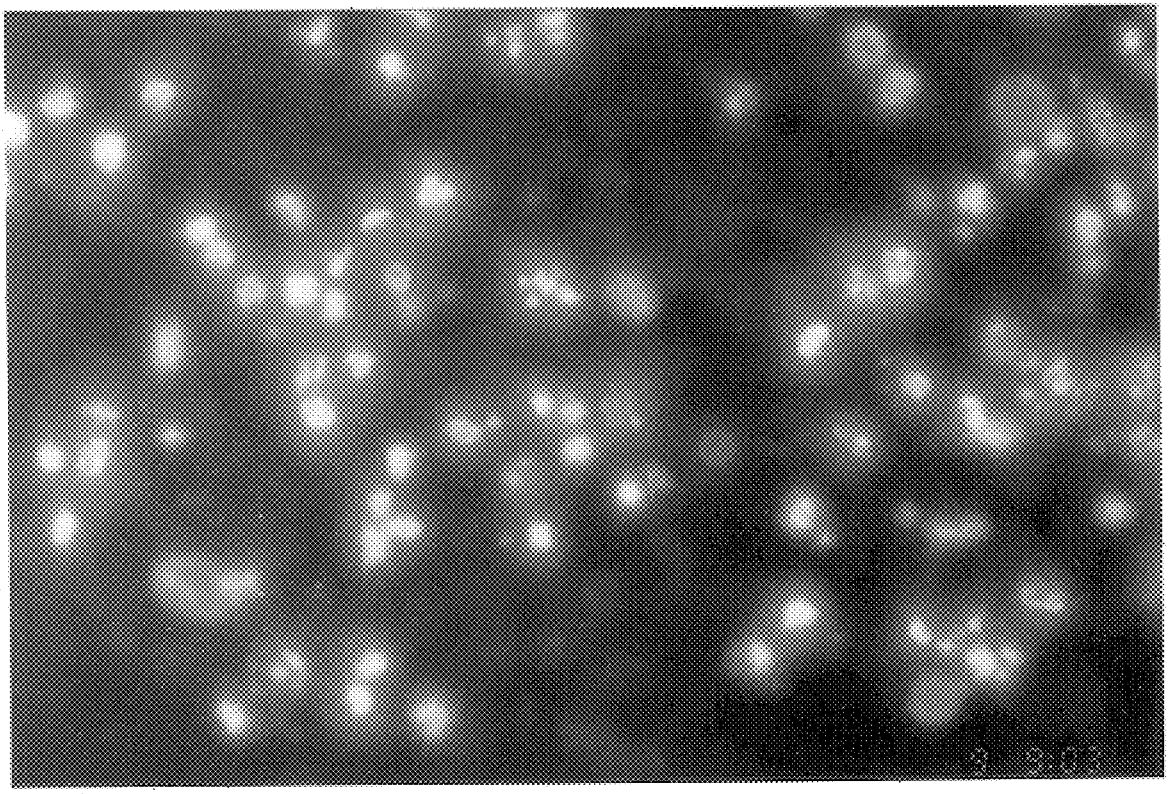

FIG. 7: Induction of apoptosis in prostate cancer cells (LNCAP) by the conditioned medium of C3H 10T1/2 cells. LNCAP cells were incubated with control medium or the conditioned medium for 15 hr and then stained with Hoechst dye for 2 hours. As shown in FIG. 7A, the nuclei of the LNCAP cells that have been incubated with control medium are normal and healthy(A). However, the nuclei of the LNCAP cells that have been incubated with the conditioned medium (X20, exchanged to RPMI) shown the characteristic of apoptosis (FIG. 7(B)). First, the conditioned medium causes the condensation of nucleus, demonstrated by the more intense fluorescent light compared with the control nucleus in FIG. 7(A). Secondly, the nucleus condensation is accompanied by the fragmentation of DNA, demonstrated by the breakage of nucleus as shown in FIG. 7(B). As we have mentioned above, the nucleus condensation and DNA fragmentation are the morphological characteristic of cells under apoptosis. These results suggest that the conditioned medium from XC cells contains an activity inducing apoptosis in LNCAP cells.

Figure 1A:
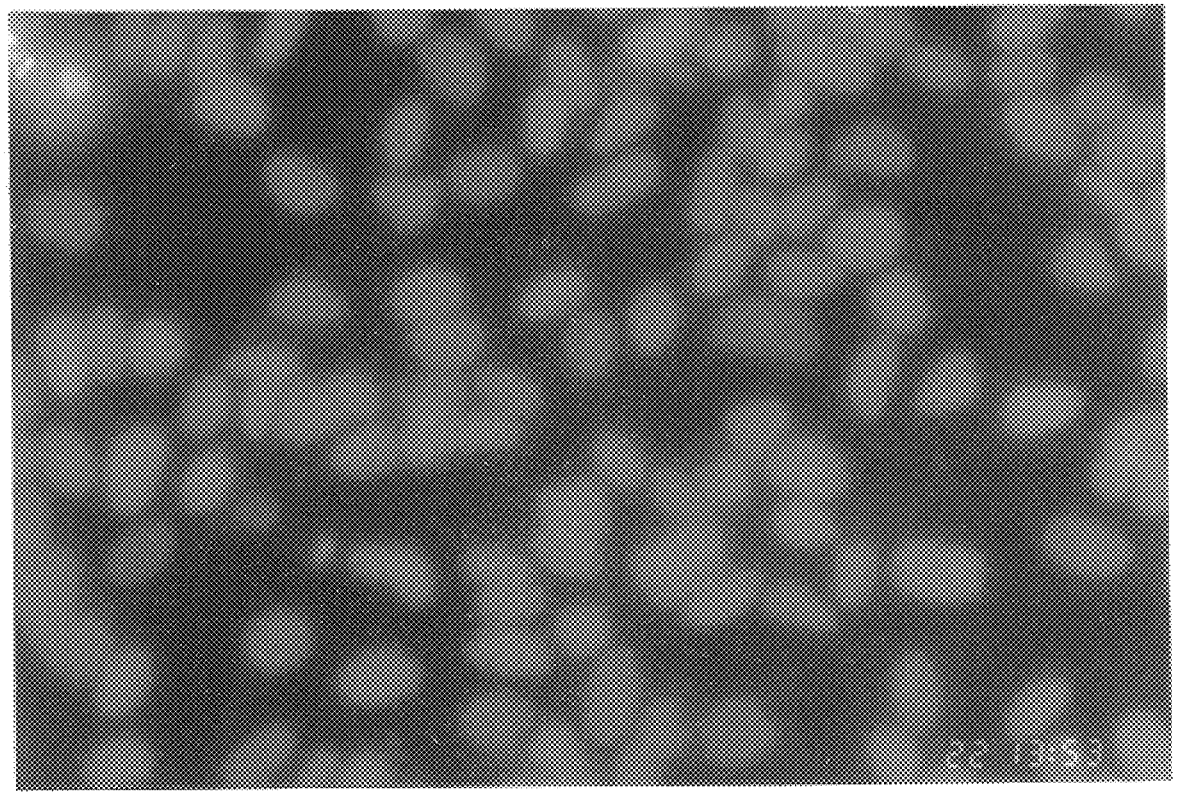
As shown in FIG. 1A, the nuclei of the LNCAP cells that have been incubated with control medium are normal and healthy (FIG. 1A). However, the nuclei of the LNCAP cells that have been incubated with the conditioned medium (X20, exchanged to RPMI) shown the characteristic of apoptosis (FIG. 1(B)). First, the conditioned medium causes the condensation of nucleus, demonstrated by the more intense fluorescent light compared with the control nucleus in FIG. 1(A). Secondly, the nucleus condensation is accompanied by the fragmentation of DNA, demonstrated by the breakage of nucleus as shown in FIG. 1(B). As we have mentioned above, the nucleus condensation and DNA fragmentation are the two morphological characteristic of cells under apoptosis. These results suggest that the conditioned medium from XC cells contains an activity inducing apoptosis in LNCAP cells.
Figure 1B:
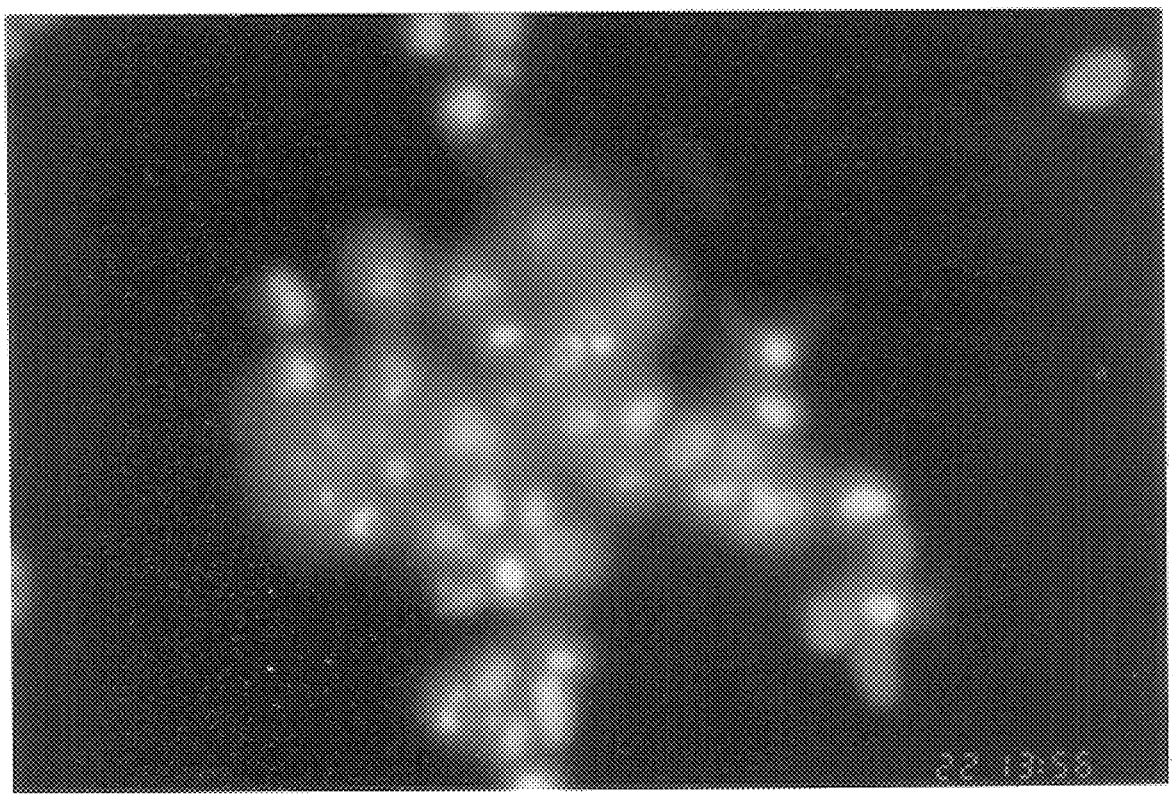
FIG. 1: Induction of apoptosis in prostate cancer cells (LNCAP) by the conditioned medium of XC cells. LNCAP cells were incubated with control medium or the conditioned medium for 15 hr and then stained with Hoechst dye for 2 hours.
Figure 2A:
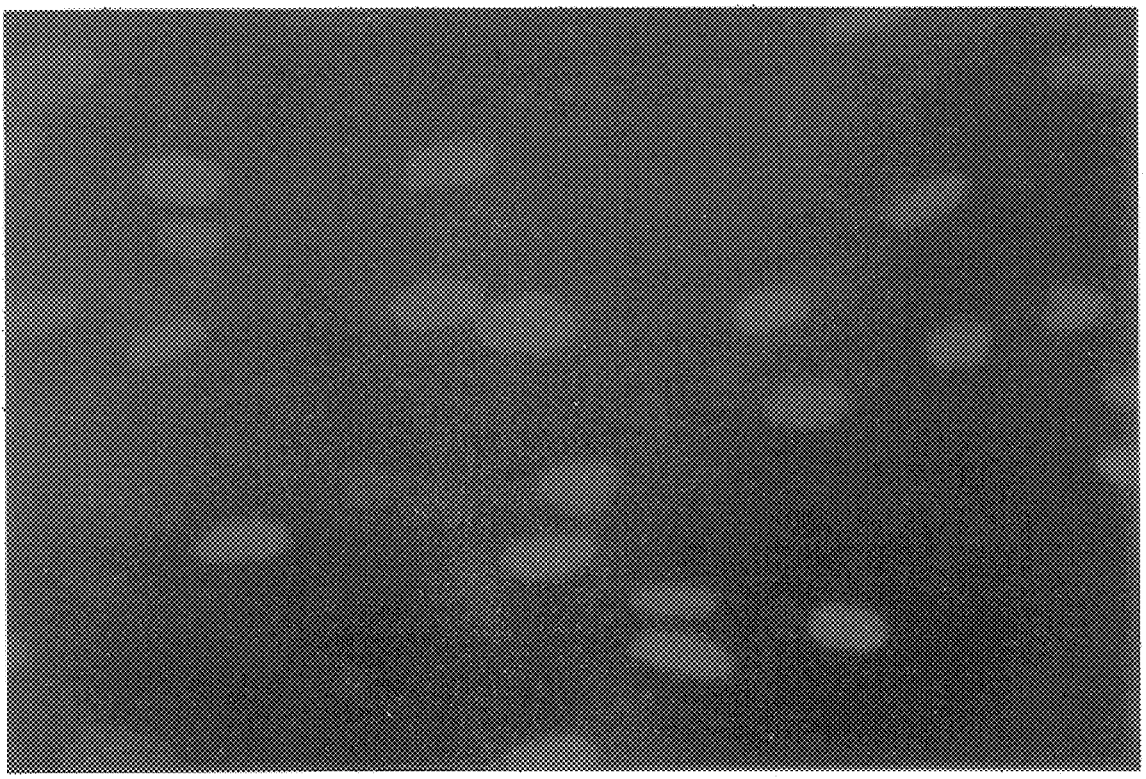
FIG. 2: The XC conditioned medium fails to induce apoptosis in normal lung fibroblast (CCD 39 Lu) cells. CCD 39 Lu cells were incubated with control medium or the conditioned medium for 15 hr and then stained with Hoechst dye for 2 hours as described in FIG. 1. Cells looked normal and healthy; the nuclei of CCD 39 Lu cells remain the same with or without incubating with the conditioned medium of XC cells (FIG. 2(A) and FIG. 2(B)). This results suggest that the XC conditioned medium fails to induce apoptosis in normal lung fibroblast (CCD 39 Lu) cells.
Figure 2B:
Figure 3:
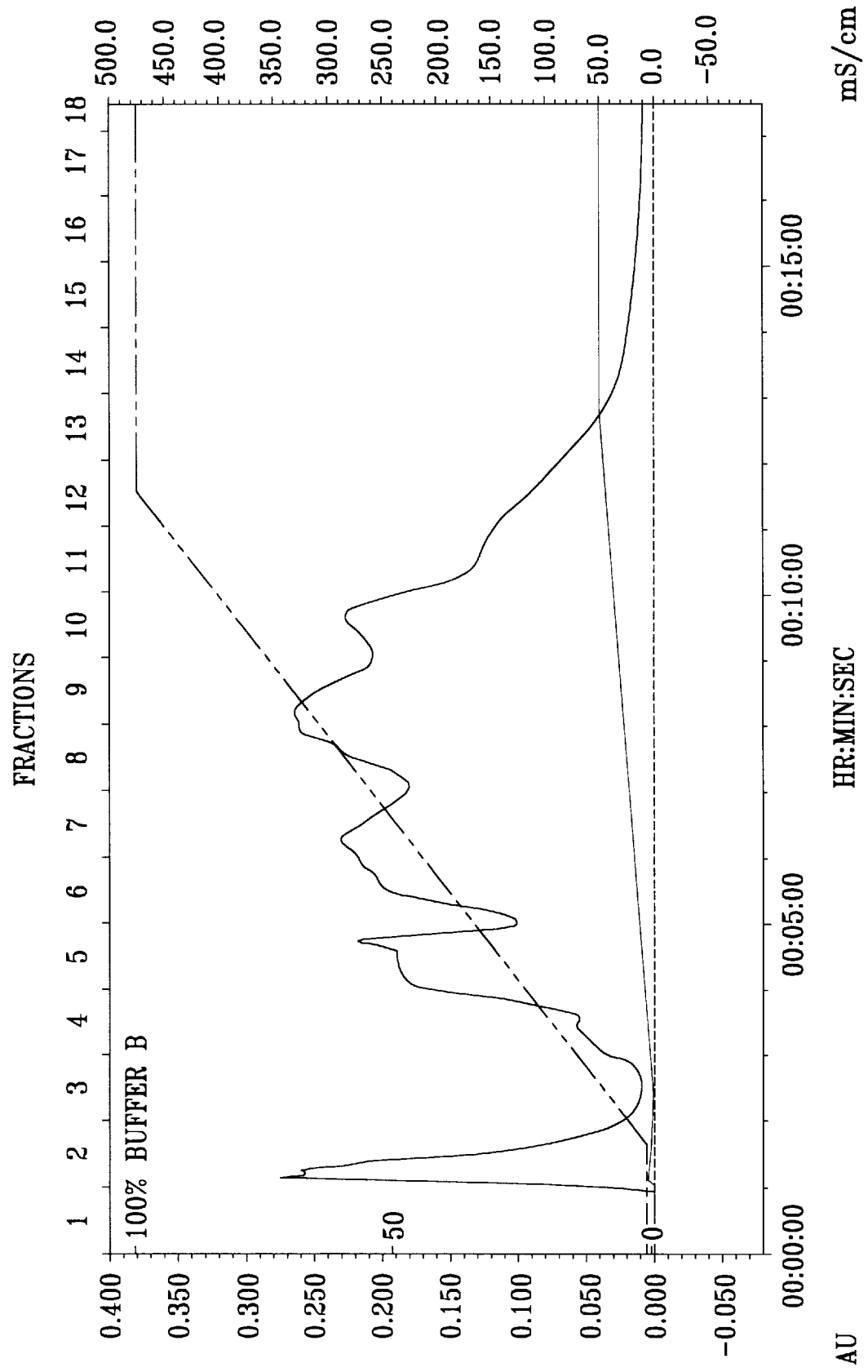
FIG. 3: Isolation of Apogen P-1s by Anion (Q2) exchange chromatography. The dissolved proteins isolated by ammonium sulfate precipitation were concentrated and loaded onto a Q2 column (Bio Rad )which is further developed by a linear gradient constructed by buffer A (10 mM Tris-HCI, pH 7.4) and buffer B (10 mM Tris-HCI, pH 7.4. 0.55 M NaCI) using BioRad's BioLogic HPLC system. The linear gradient was constructed by increasing buffer B from 0% to 100% in buffer A within 10 min (20 milliliter elution volume and thereafter the column was eluted with 100% buffer B for 5 min. The Apogen P-1 activity was assayed by the induction of apoptosis in LNCAP cells. We found that there are three activity peaks across the chromatogram profile. Fraction 5 to 7 cause 70% cell death, fraction 8–10 cause 65% cell death and fraction 11–14 caused 90% cell death in 18 Hr. We collected fractions 5–7 and named it Apogen P-1a, fractions 8–10 is named Apogen P-1b and fractions 11–14 is named Apogen P-1c. These three Apogen P-1s were further purified by a reverse phase column.
Figure 8A:
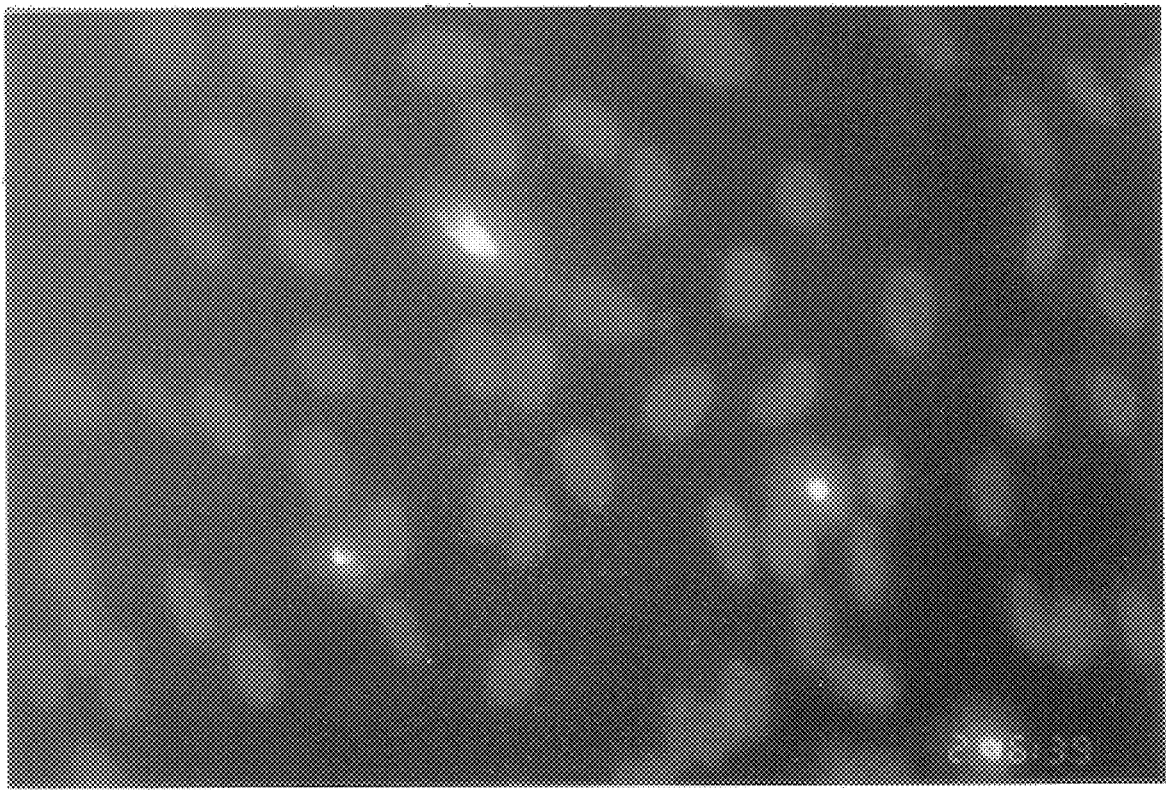
Figure 8B:
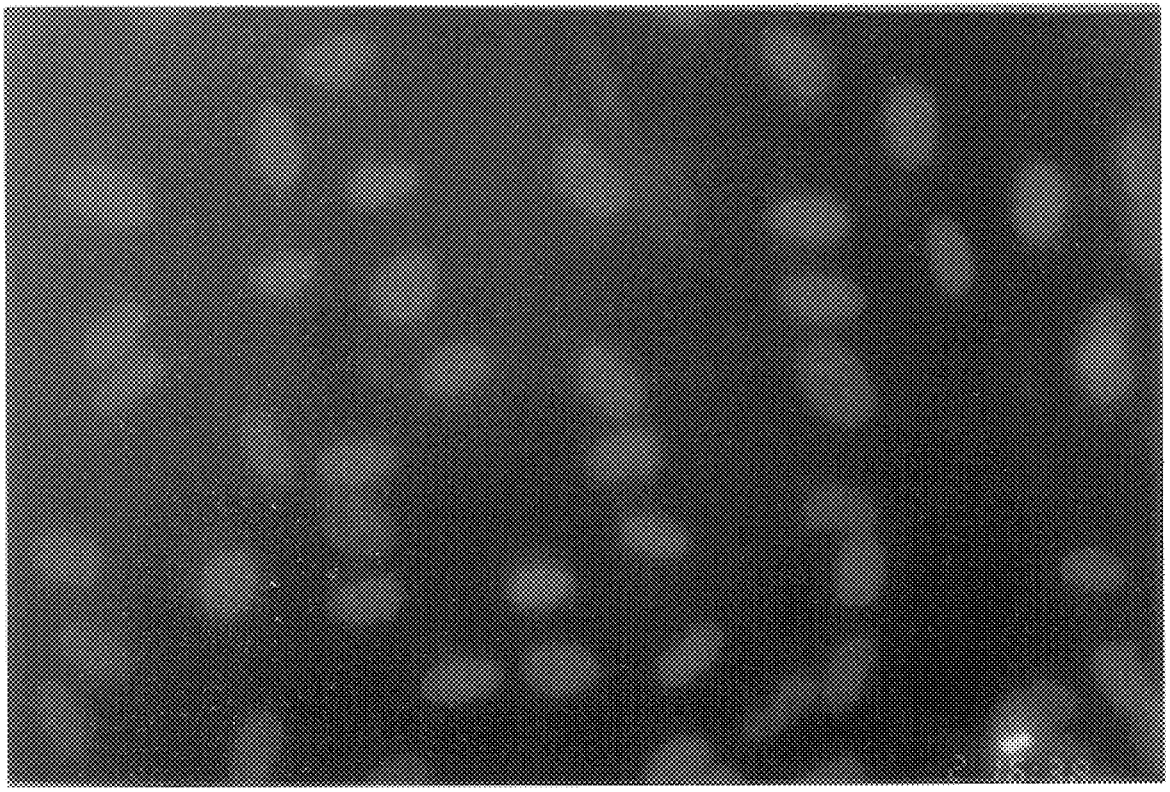

FIG. 8: The C3H 10T1/2 conditioned medium fails to induce apoptosis in normal lung fibroblast (CCD 39 Lu) cells. CCD 39 Lu cells were incubated with control medium or the conditioned medium for 15 hr and then stained with Hoechst dye for 2 hours as described in FIG. 1. Cells looked normal and healthy; the nuclei of CCD 39 Lu cells remain the same with or without incubating with the conditioned medium of C3H 10T1/2 cells (FIG. 8(A) and FIG. 8(B)). This results suggest that the C3H 10T1/2 conditioned medium fails to induce apoptosis in normal lung fibroblast (CCD 39 Lu) cells.

Figure 9:
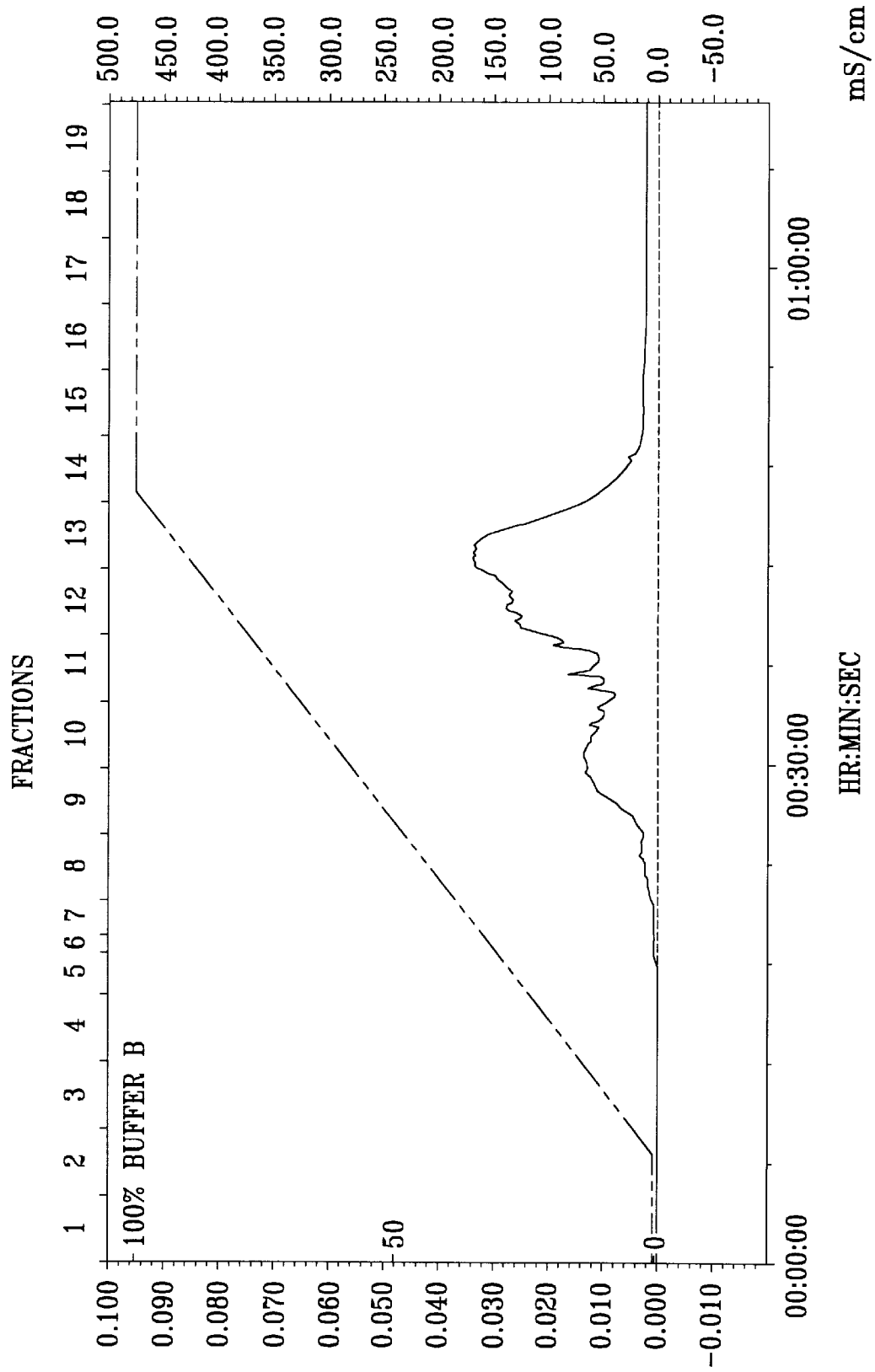

FIG. 9: Reverse phase chromatography of Apogen P-2. Apogen P-2 that has been purified by DE52 cellulose, hydroxylapatite and heparin agarose was further purified by a reverse phase chromatography. Apogen P-2 was concentrated to 1 ml. One milliliter of methanol containing 0.05% trifluoracetic acid was added. Large amount of proteins were precipitated by this treatment Whereas, the apoptosis inducing activity (P-2) remained in supernatant. The supernatant was then applied to a reverse phase RP-4 column (Micra Scientific Inc) and developed by a linear gradient constructed by solution A ($H_2O$, 0.05% TFA) and solution B (Methanol, 0.05% TFA). The linear gradient was constructed by increasing solution B from 0% to 100% in solution A within 10 min (20 milliliter elution volume and thereafter the column was eluted with 100% solution B for 5 min.

Figure 10:
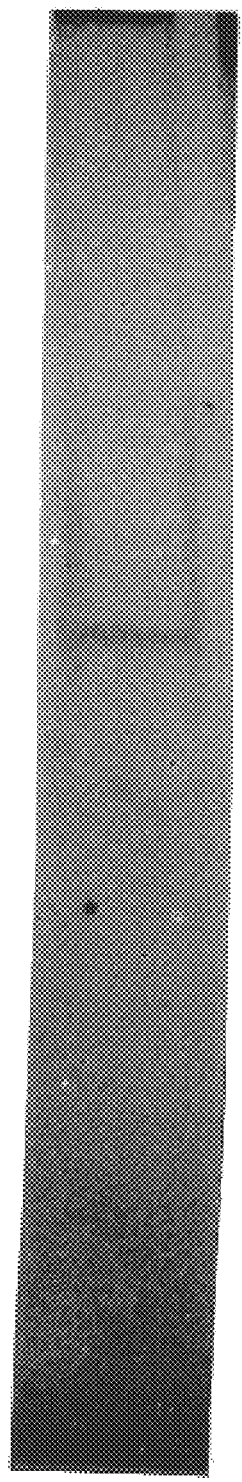

FIG. 10: Apogen P-2 isolated by anion exchange chromatography and reverse phase chromatography was concentrated and subjected to electrophoresis under denaturing conditions through a 4–20% gradient SDS-Polyacrylamide gel. The gel was silver stained. A protein band with molecular weight of 65 KD was obtained. This result suggest the successful purification of Apogen p-2 which have molecular weight of 65 KD on SDSPAGE.

Figure 11:
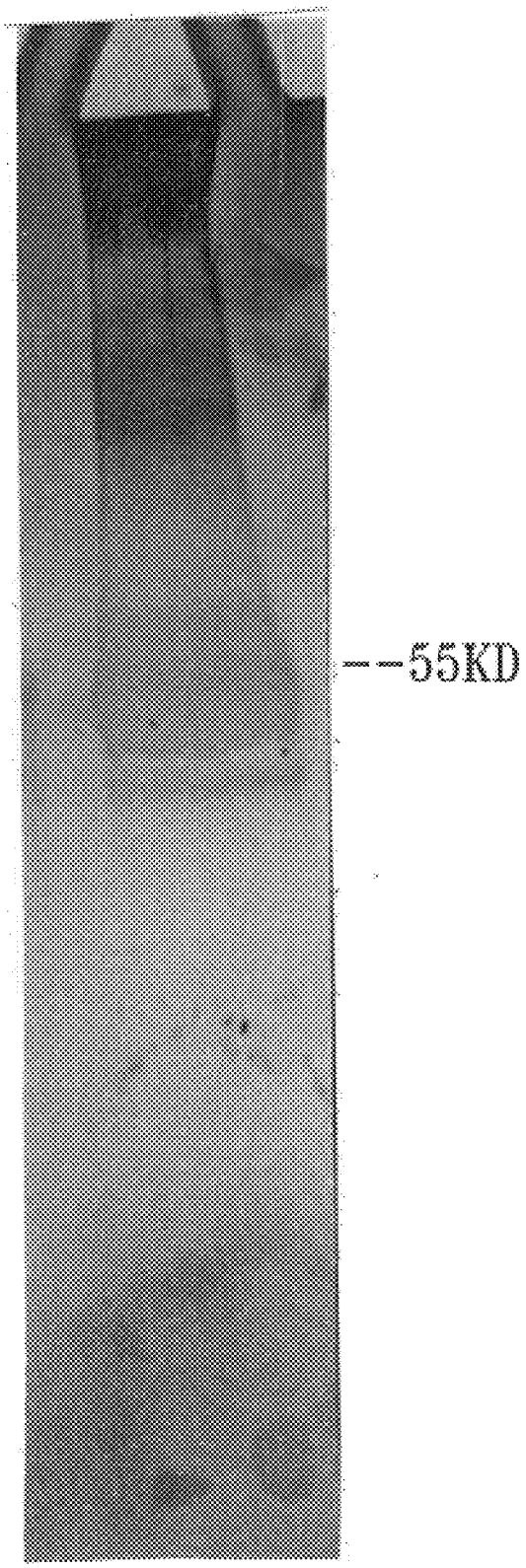

FIG. 11: Apogen L isolated by anion exchange chromatography and reverse phase chromatography was concentrated and subjected to electrophoresis under denaturing conditions through a 4–20% gradient SDS-Polyacrylamide gel. The gel was silver stained. A protein band with molecular weight of 55 KD was obtained.

Figure 12:
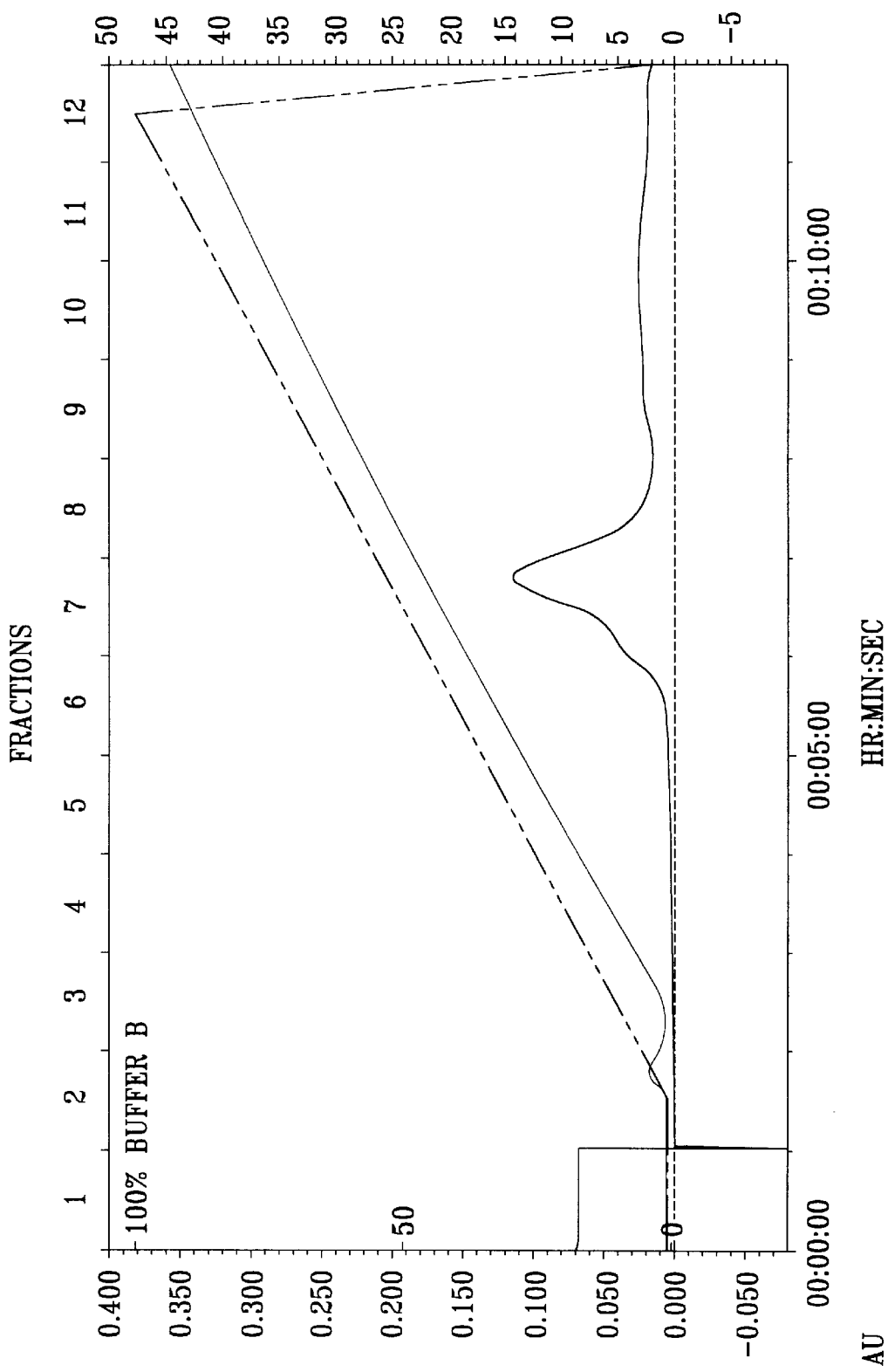

FIG. 12: Anion exchange chromatography of Apogen L. Apogen L isolated by DE 52 cellulose, heparin agarose was concentrated and loaded onto a Q2 column (Bio-Rad )which is further developed by a linear gradient constructed by buffer A (10 mM Tris-HCI, pH 7.4) and buffer B (10 mM Tris-HCI, pH 7.4. 0.5 M NaCI) using Bio-Rad's BioLogic HPLC system. The linear gradient was constructed by increasing buffer B from 0% to 100% in buffer A within 10 min. Fractions 7 and 8 contain activity inducing apoptosis in HL-60 cells.

Figure 13A:
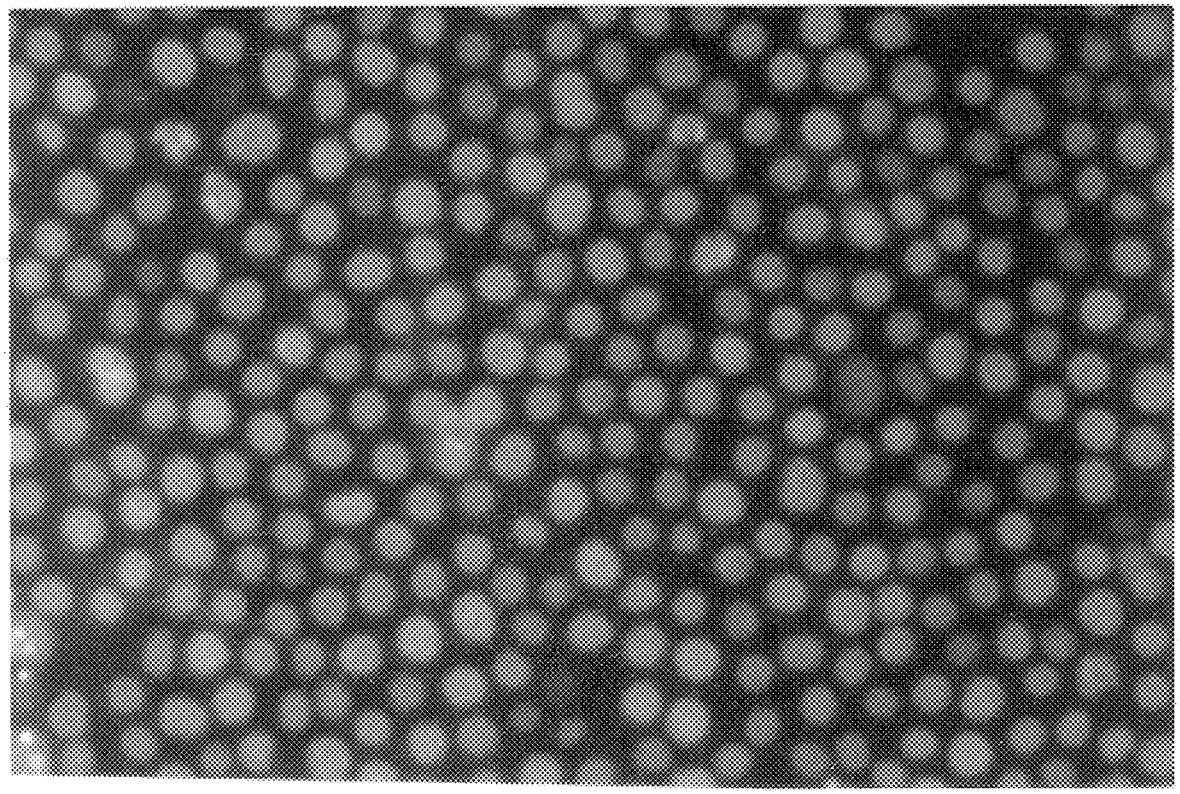
Figure 13B:
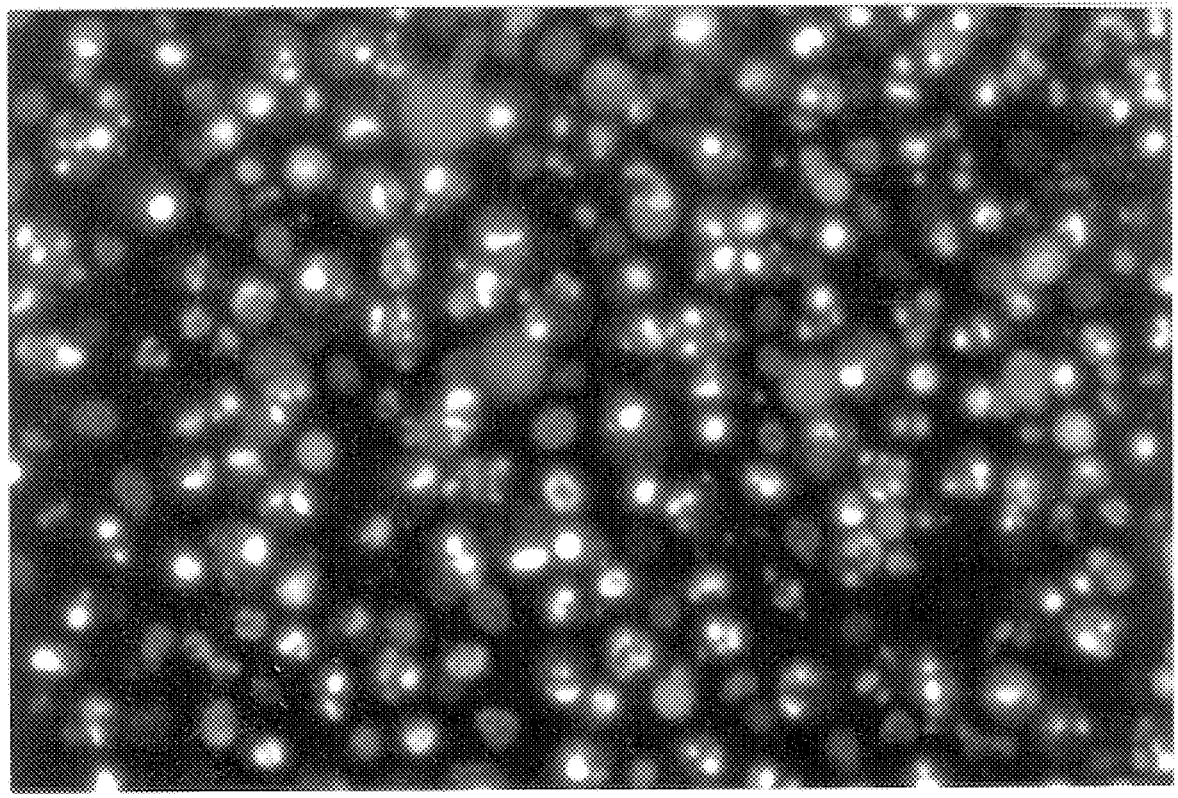

FIG. 13: induction of apoptosis in HL-60 cells by Apogen L. The activity of Apogen L isolated by DE 52 cellulose, heparin agarose and anion exchange chromatography was tested on the following cell lines: HL-60 (leukemia) and CCD 39 Lu (normal lung fibroblast). To morphologically demonstrated that Apogen L contains activity inducing apoptosis, HL-60 cells were incubated with Apogen L isolated as described as above for 15 hr and then stained with Hoechst dye for 2 hours. As shown in FIG. 13A, the nuclei of the HL-60 cells that have been incubated with control medium are normal and healthy(A). However, the nuclei of the HL-60 cells that have been incubated with Apogen L shown the characteristic of apoptosis (FIG. 13B). First, Apogen L causes the condensation of nucleus, demonstrated by the more intense fluorescent light compared with the control nucleus in FIG. 13A. Secondly, the nucleus condensation is accompanied by the fragmentation of DNA, demonstrated by the breakage of nucleus as shown in FIG. 13B. As we have mentioned above, the nucleus condensation and DNA fragmentation are the two morphological characteristic of cells under apoptosis. These results suggest that the isolated Apogen L contains an activity inducing apoptosis in HL-60 cells.

Figure 14A:
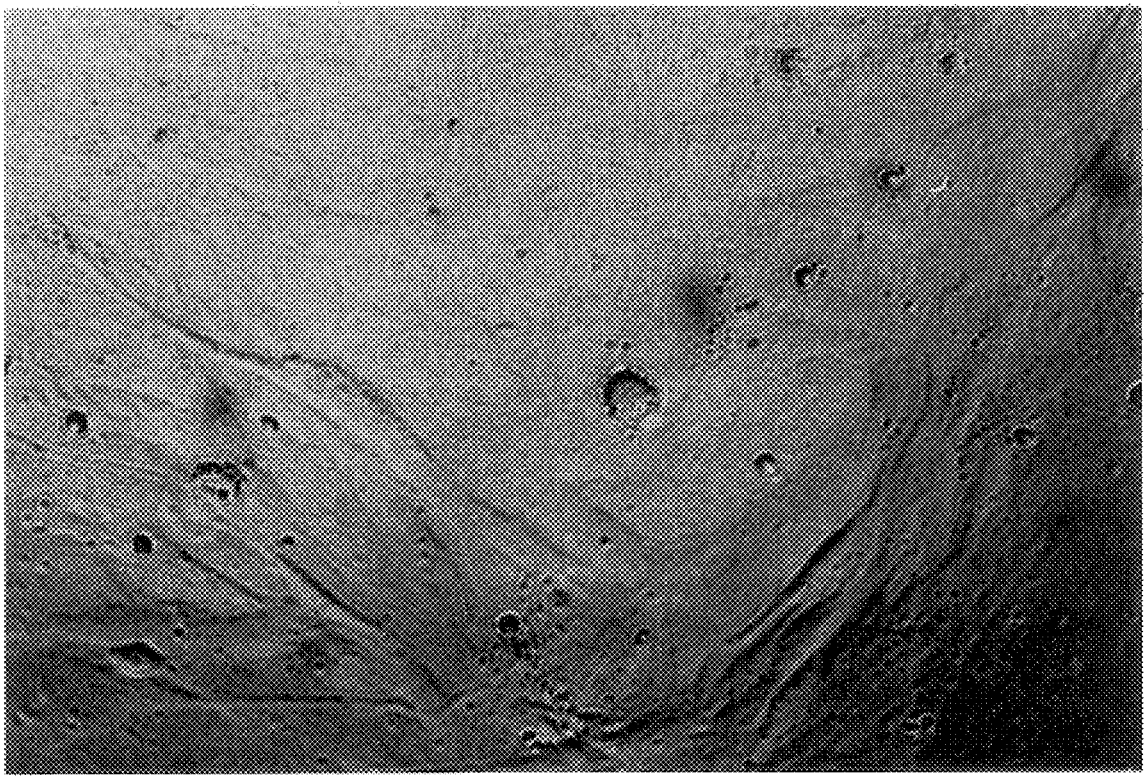
Figure 14B:
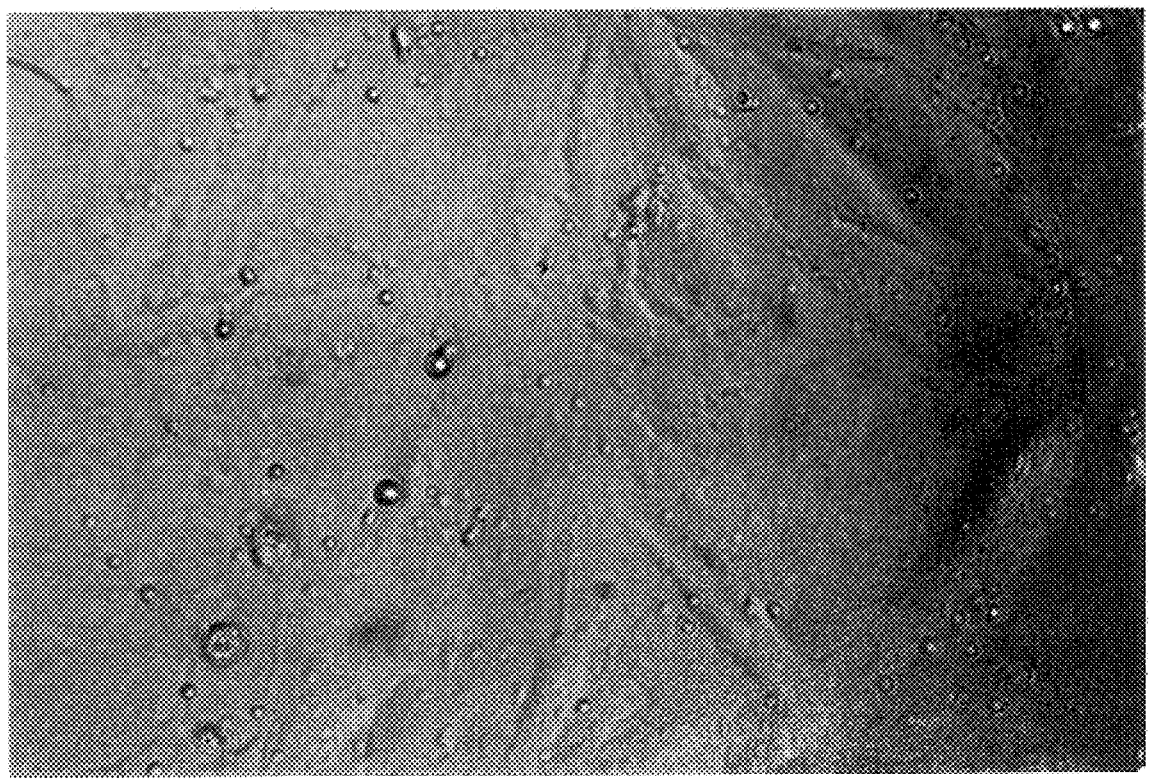

FIG. 14: induction of apoptosis in MCF-7 cells by Apogen L. The activity of Apogen L isolated by DE 52 cellulose, heparin agarose and anion exchange chromatography was tested on the following cell lines: MCF-7 (breast cancer cells). To morphologically demonstrated that Apogen L contains activity inducing apoptosis, MCF-7 cells were incubated with Apogen L isolated as described as above for 15 hr. As shown in FIG. 14A, the nuclei of the MCF-7 cells that have been incubated with control medium are normal and healthy(A). However, the nuclei of the MCF-7 cells that have been incubated with Apogen L shown the characteristic of apoptosis (FIG. 14B). These results suggest that the isolated Apogen L contains an activity inducing apoptosis in MCF-7 cells.

Figure 15A:
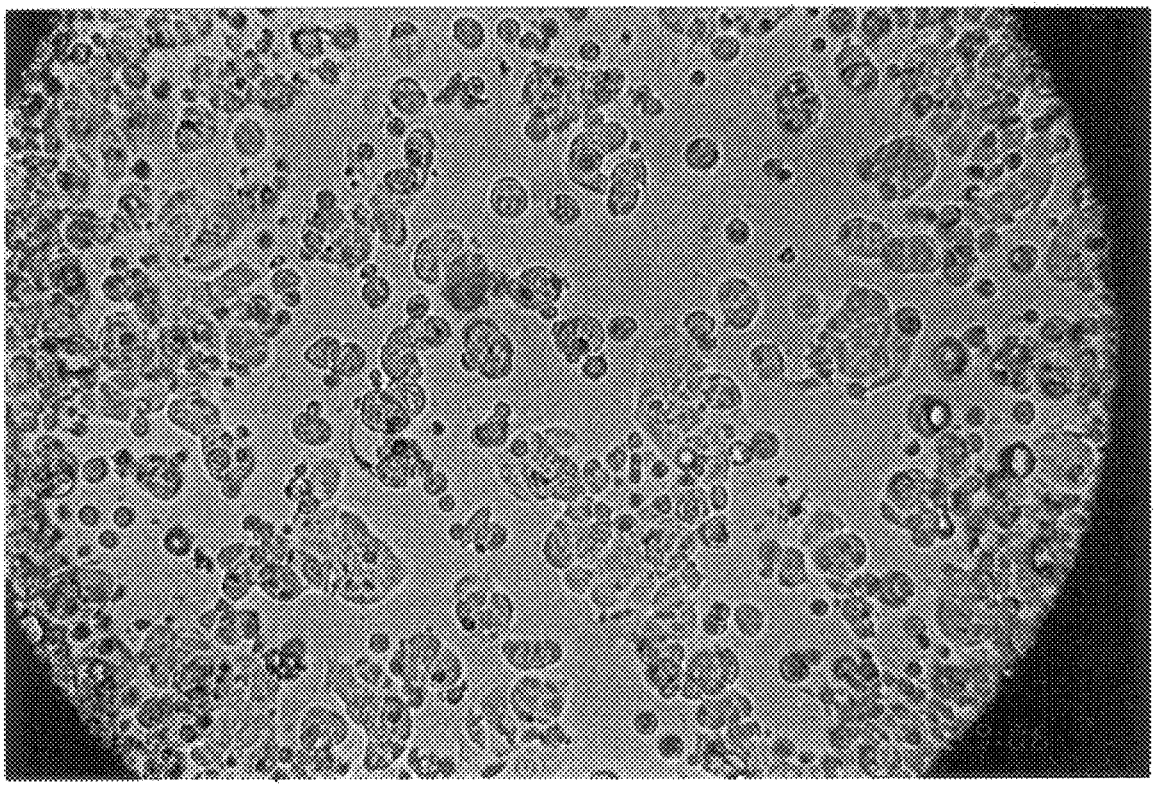
Figure 15B:
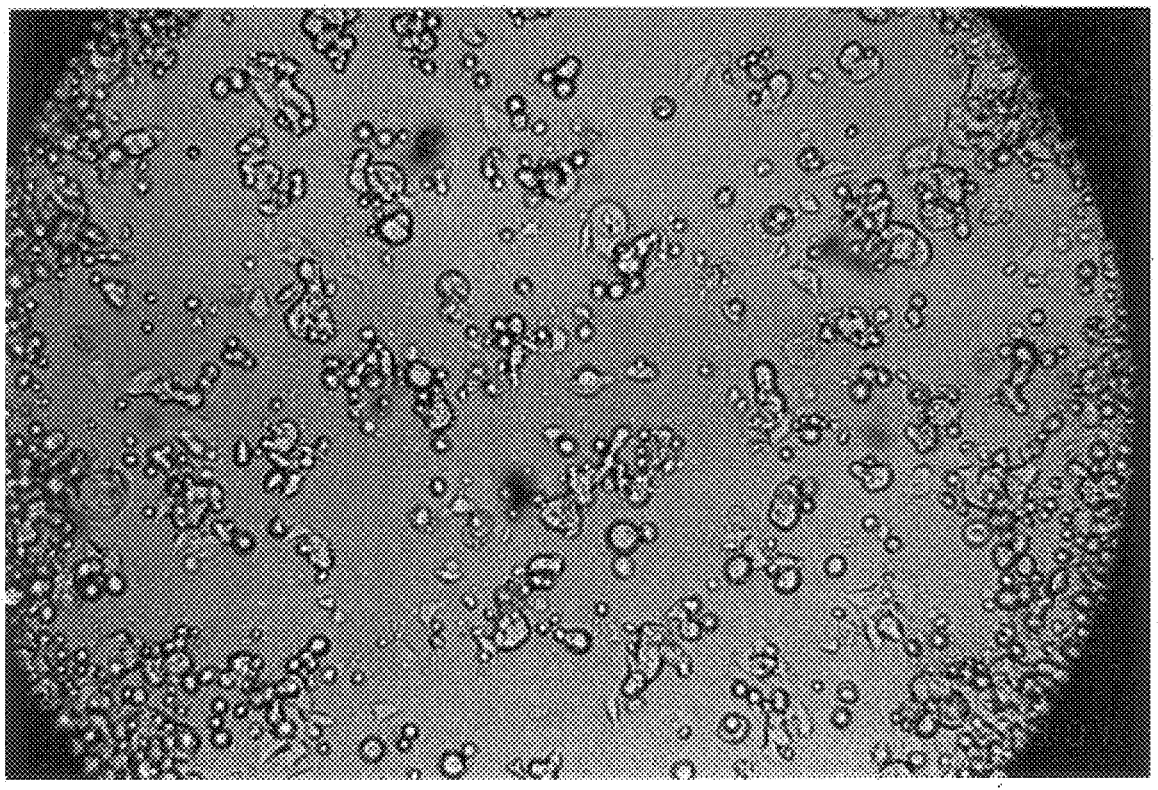

FIG. 15: Apogen L fails to induce apoptosis in normal breast cells (Hs578 Bst) cells in MEM-insulin-10% serum medium. Hs578 Bst cells were incubated with control medium or the conditioned medium for 15 hr. Cells looked normal and healthy; the nuclei of Hs578 Bst cells remain the same with or without incubating with Apogen L. These results suggest that Apogen L fails to induce apoptosis in normal breast cells (Hs578 Bst).

Figure 16A:
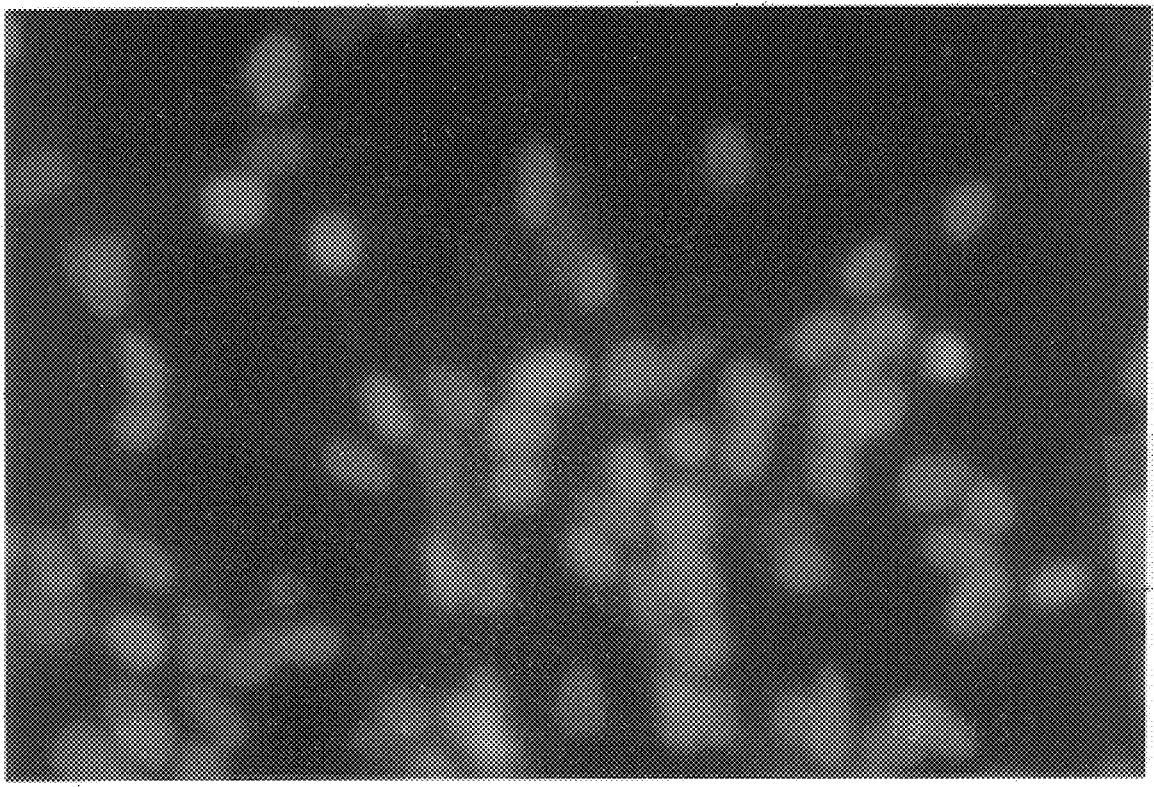
Figure 16B:
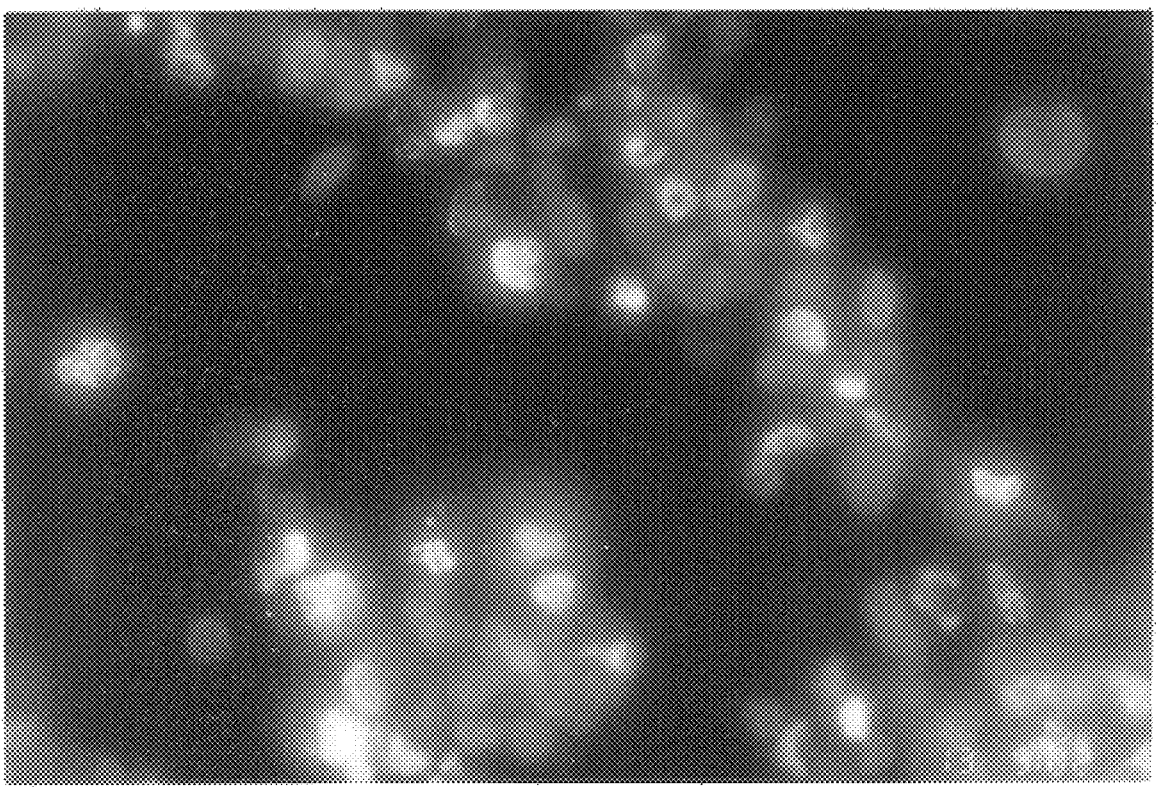

FIG. 16: Incubation of LNCaP cells with control sample (PBS) fails to induce apoptosis (FIG. 16(A)). Incubation of LNCaP cells with fetuin (25 $\mu$g/ml in PBS) show the characteristics of apoptosis, including condensation of the nucleus and fragmentation of DNA (FIG. 16(B)).

Figure 17A:
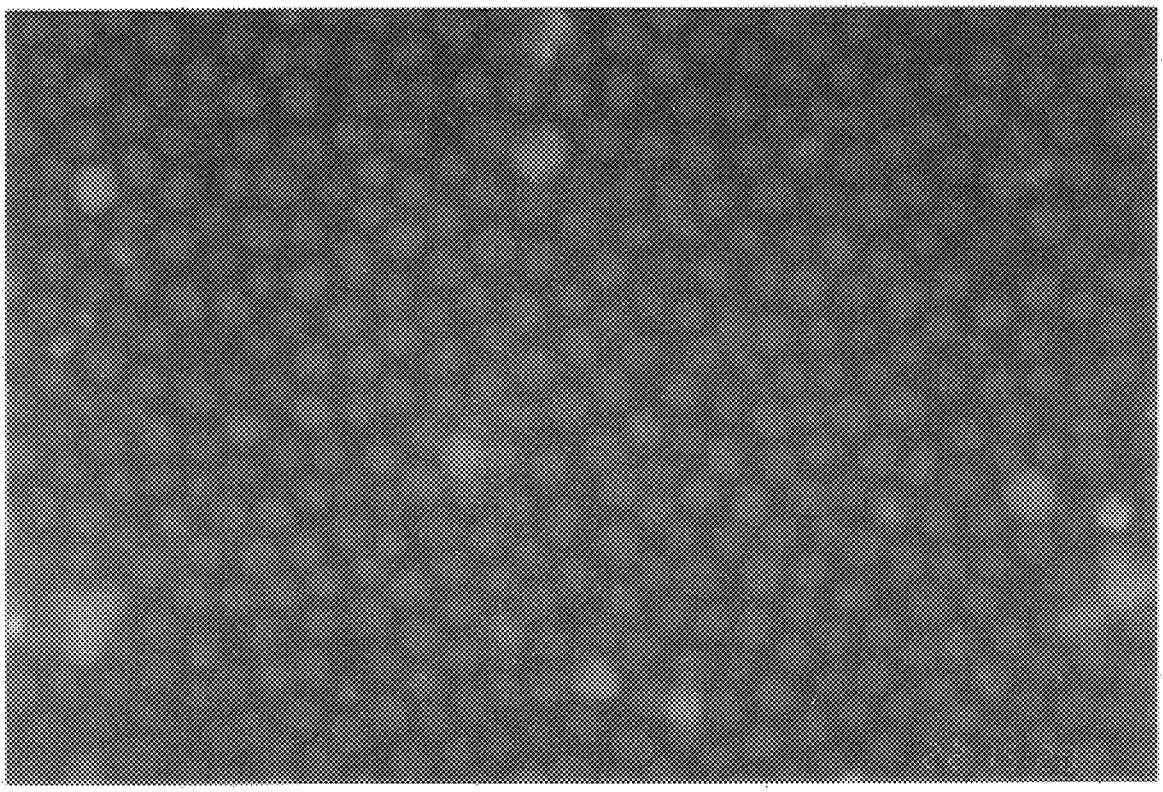
Figure 17B:
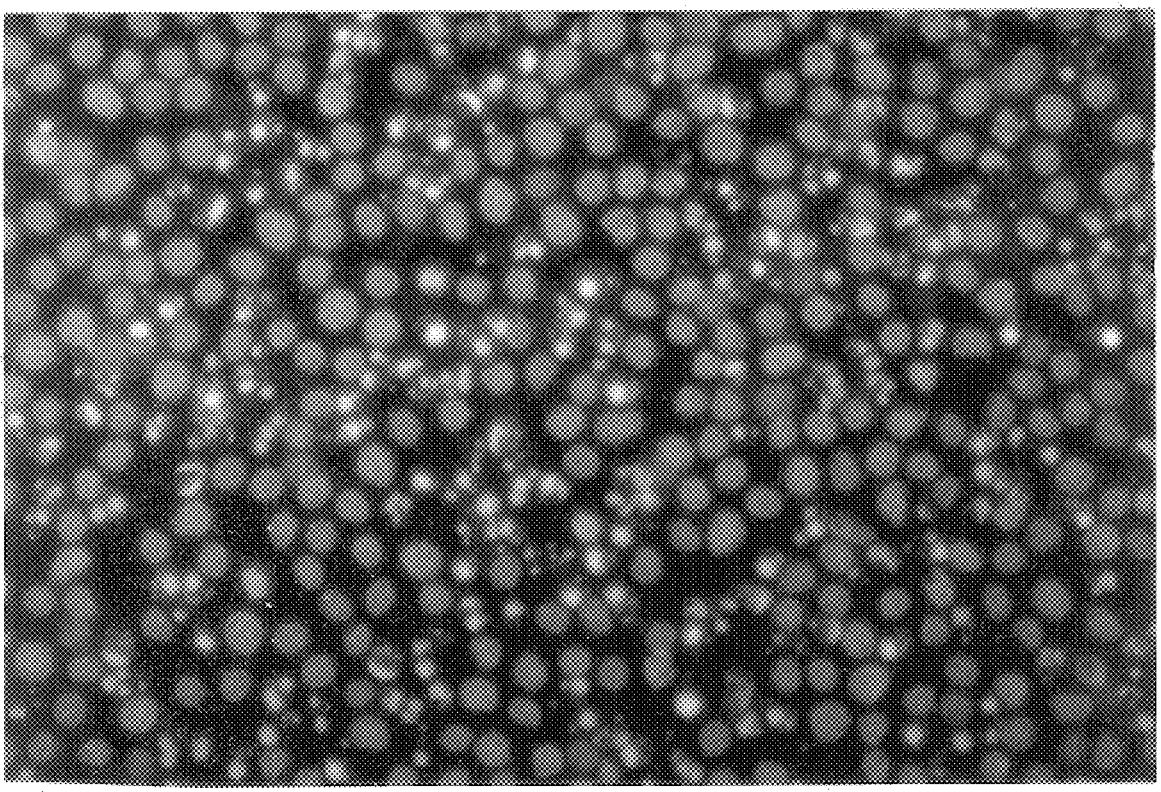

FIG. 17: Incubation of HL-60 cells with control buffer (PBS) fails to induce apoptosis (FIG. 17(A)). Incubation of HL-60 cells with fetuin causes apoptosis, with cells exhibiting condensation of the nucleus and fragmentation of DNA (FIG. 17(B)).

Figure 18:
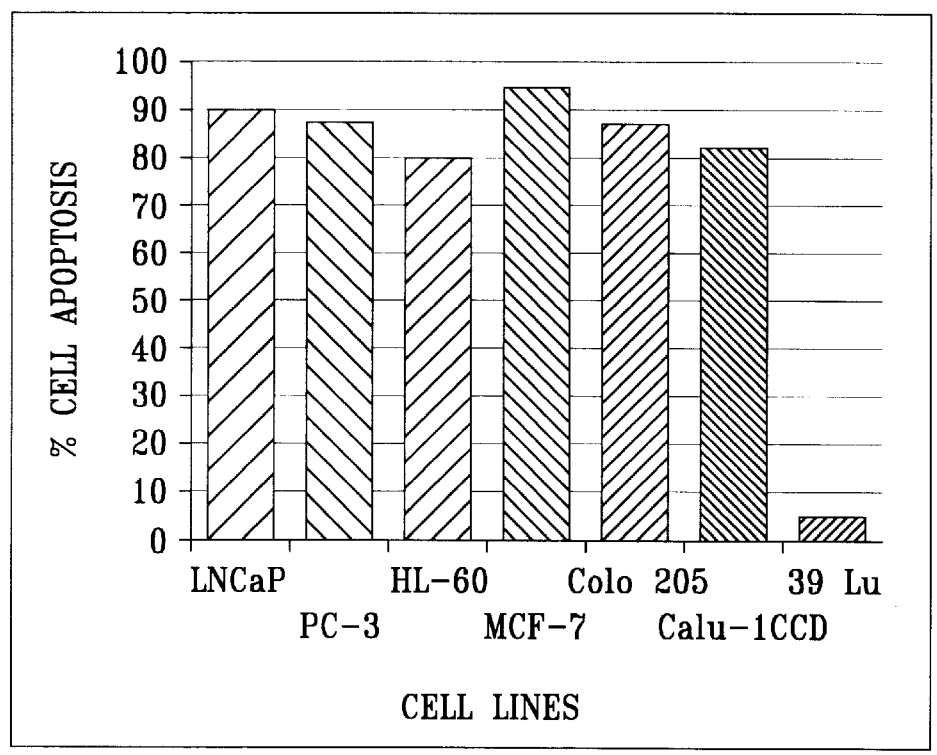

FIG. 18: Fetuin prepared by the method described in section 4.A. at a concentration of 20 ng/ml induces apoptosis in tumor cells lines LNCaP, PC-3, HL-60, MCF-7, Colo 205, and Calu-1, while not inducing apoptosis in normal lung fibroblasts (CCD 39 Lu).

Figure 19A:
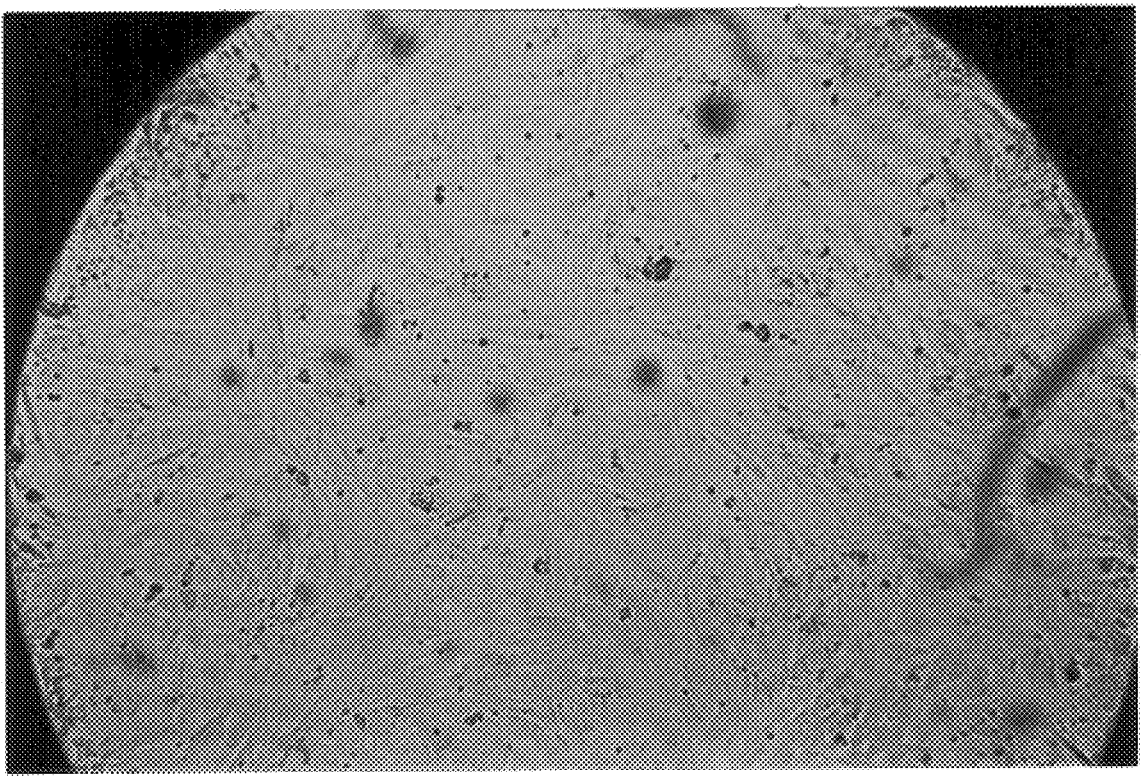

FIG. 19: CCD 39 Lu cells incubated with Fetuin (25 $\mu$g/ml) for 15 hours remained morphologically unchanged.

Figure 20A:
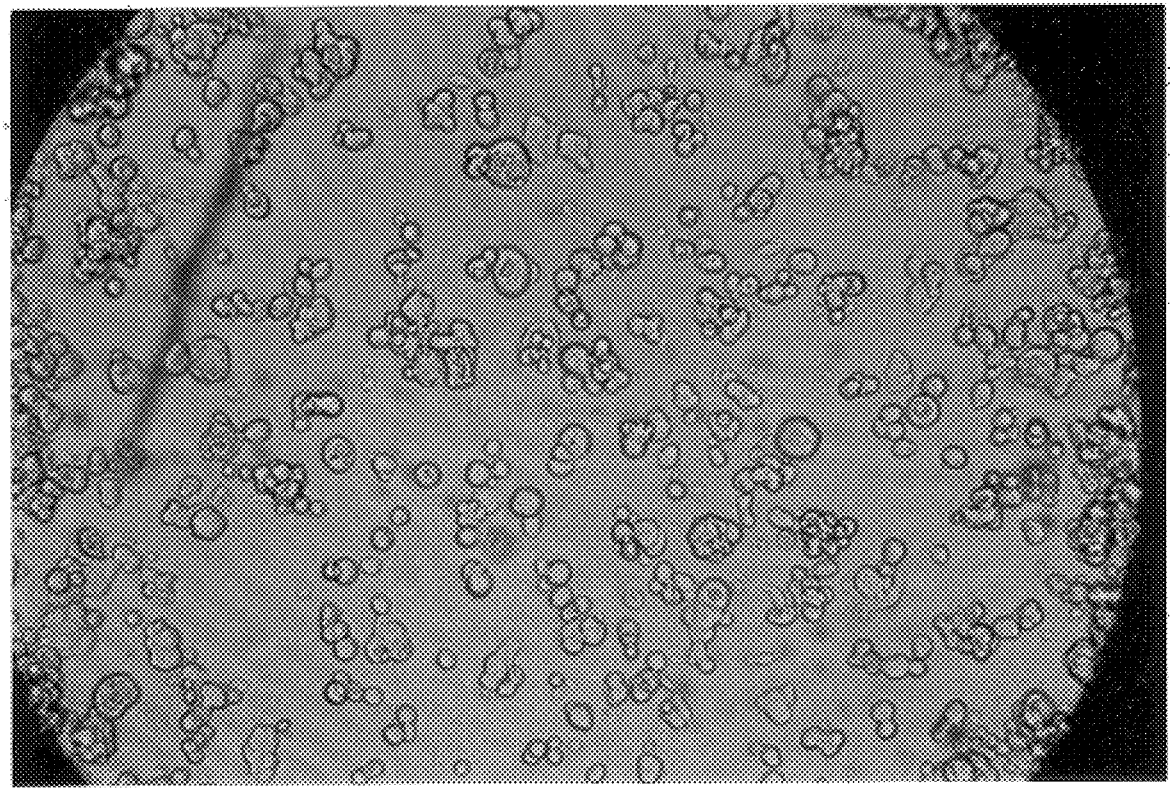

FIG. 20: Fetuin at a concentration of 25 $\mu$g/ml induces apoptosis in breast cancer cells (MCF-7).

EXAMPLES

A. Methods

1. Preparation of Condition Media

A. Preparation of XC Condition Medium for Isolation of Apogen p-1

Apogen P-1 was isolated from the conditioned medium of a cell line called XC which was derived from rat tumor (ATCC CCL 165). XC cells were first seeded in roller bottle (Polystyrene, area surface=850 $Cm^2$, Corning) in Dulbecco's Modification of Eagle's Medium (DMEM) containing $CO_2$, 10% fetal bovine serum (FBS), non-essential amino acids, penicillin and streptomycin for 3 days. XC cells were then washed with PBS (3×100 ml) to remove serum and then grown in 100 ml of DMEM containing no FBS (with $CO_2$), non-essential amino acids, penicillin and streptomycin) for 4 days. The conditioned medium was collected and clarified by centrifugation.

B. Preparation of C3H 10T1/2 Condition Medium for Isolation of Apogen P-2

Apogen P-2 was isolated from the conditioned medium of a cell line called C3H10T1/2 which was derived from mouse embryo and is purchased from American Type Culture Collection (ATCC CCL 226). C3H 10T1/2 cells were first seeded in roller bottle (Polystyrene, area surface=850 $Cm^2$, Corning) in alpha Modification of Eagle's Medium (alpha-MEM) containing $CO_2$, 10% Fetal bovine serum (FBS), penicillin and streptomycin for 3 days. C3H 10T1/2 cells were then washed with PBS (3×100 ml) to remove serum and then grown in 100 ml of alpha MEM containing no FBS (with $CO_2$, penicillin and streptomycin) for 4 days. The conditioned medium was collected and clarified by centrifugation.

C. Preparation of XC Condition Medium for Isolation of Apogen L

Apogen L was isolated from the conditioned medium of a cell line called XC which was derived from rat tumor (ATCC CCL 165). XC cells were first seeded in roller bottle (Polystyrene, area surface=850 $Cm^2$, Corning) in Dulbecco's Modification of Eagle's Medium (DMEM) containing penicillin, streptomycin, $CO_2$, non-essential amino acids and 10% Fetal bovine serum (FBS) for 4 days. The conditioned medium was collected and clarified by centrifugation.

2. Assays (a) Cell Death (Apoptosis) Assay

Prostate cancer cell line LNCAP was routinely used for the isolation of Apogen P-1 and Apogen P-2, whereas leukemia cell line HL-60 was used for the isolation of Apogen L. The methods of assays are as following: LNCAP or HL-60 (1,000 cells) was seeded in 10 microliters RPMI containing 15% or 20% Fetal bovine serum, penicillin and streptomycin at 37 degree, 5% $CO_2$ in Microtray plates (25 $\mu$l wells, Robbins Scientific Corp.). Tested sample (10 $\mu$l) was added 3–4 hours after cells were seeded. After incubation of the tested sample with cells for 15 hours, two microliters of Hoechst dye (0.03 ng/ml in PBS) was added. Two hours later, cells that were stained with Hoechst dye were examined under fluorescence microscope. The nuclei of apoptotic cells showed DNA condensation and fragmentation are easily be identified by Hoechst dye staining. The percentage of apoptotic cells was calculated by the following equation:

% Apoptotic cells=Number of cells with DNA condensation and fragmentation/Total cell number (b) Cell Repelling Assay There are two reasons that Hep G2 cells are chosen for the study of cell repelling activity. First, Hep G2 cells are not sensitive to Apogen P-1 in inducing apoptosis. Secondly, the cell size of Hep G2 cell is about 3–4 times as big as the pore size of the membrane on the Transwell Insert, which is a good cell size for cell migration/invasion study. A tissue culture device called Transwell Insert purchased from Costar (Cambridge, Mass.) was used to discover the chemorepellent activity of Apogen P-1b. This device, which has been widely used for the studies of cell migration/invasion, contains an upper chamber and a lower chamber. Between these two chambers is a polyester microporous membrane with 3.0 um pore size which allows cell to migrate through the membrane. Tested cells were grown on the upper chamber and tested compound is placed in the lower chamber. If this tested compound is a chemoattractant, we should see more cells migrate through membrane than the control sample. In our experiments, Hep G2 (100,000 cells) cells, which have cell size 3–4 times as big as the membrane pore size were grown in the upper chamber (Minimum Essential Medium Eagle containing 10% FBS, PS and nonessential amino acid, 0.1 ml) for 2 hours and then the partially purified Apogen-1b (30 μl) isolated by ammonium sulfate precipitation and Q2 HPLC chromatography as described above was placed in the lower chamber which contains 0.6 ml of the same growth medium for Hep G2 cells. After 15 hours, cells that have migrated through the membrane were collected by treating the membrane with 0.2 ml of trypsin solution for 30 min. Cells in ten microliters of the trypsin solution were counted in a Hemacytometer.

3. Protein Isolation

A. Isolation of Apogen P-1

Step 1: Ammonium Sulfate Precipitation

Apogen P-1 was precipitated by 80% saturated of ammonium sulfate by adding 561 g of ammonium sulfate per liter of XC conditioned medium. Pellet was collected by centrifugation and the proteins were dissolved in 10 mM Tris-HCI (pH 7.4). After removal of ammonium sulfate by dialysis, the dissolved proteins were separated by a Q2 HPLC column.

Step 2: Q2 HPLC Chromatography

The dissolved proteins isolated by ammonium sulfate precipitation were concentrated and loaded onto a Q2 column (Bio Rad )which is further developed by a linear gradient constructed by buffer A (10 mM Tris-HCI, pH 7.4) and buffer B (10 mM Tris-HCI, pH 7.4. 0.55 M NaCl) using BioRad's BioLogic HPLC system. The linear gradient was constructed by increasing buffer B from 0% to 100% in buffer A within 10 min (20 milliliter elution volume) and thereafter the column was eluted with 100% buffer B for 5 min. The Apogen P-1 activity was assayed by the induction of apoptosis in LNCAP cells. We found that there are three activity peaks across the chromatogram profile. Fraction 5 to 7 cause 70% cell death, fraction 8–10 cause 65% cell death and fraction 11–14 caused 90% cell death in 18 Hr. We collected fractions 5–7 and named it Apogen P-1a, fractions 8–10 is named Apogen P-1b and fractions 11–14 is named Apogen P-1c. These three Apogen P-1's were further purified by a reverse phase column.

Step 3: Reverse Phase Chromatography

Apogen P-1a, Apogen P-1b and Apogen P-1c were separately concentrated to 1.5 ml. One ml of methanol containing 0.05% Trifluoracetic acid was added. In each samples, large amount of proteins were precipitated by this treatment.

Whereas, the apoptosis inducing activity remained in supernatant. The supernatant was then applied to a reverse phase RP-4 column (Micra Scientific Inc) and developed by a linear gradient constructed by solution A ($H_2O$, 0.05% TFA) and solution B Methanol, 0.05% TFA). The linear gradient was constructed by increasing solution B from 0% to 100% in solution A within 10 min 20 milliliter elution volume and thereafter the column was eluted with 100% solution B for 5 min.

Step 4: Preparative Electrophoresis

Apogen 1c isolated by anion exchange chromatography was purified by both Reverse phase chromatography (step 3) and Preparative Electrophoresis by a MiniPrep Gel electrophoresis (Bio-Rad). The reverse phase chromatogram of Apogen P-1a is shown in FIG. 4(a). fractions 12–13 have activity inducing 80% cell death in LNCAP cells at 10 hr.

The reverse phase chromatogram of Apogen P-1b is shown in FIG. 4(b). fractions 14 and 15 have activity inducing 45% cell death in LNCAP cells at 18 hr.

The reverse phase chromatogram of Apogen P-1c is shown in FIG. 4(c). fraction No 5 have activity inducing 52% cell death in LNCAP cells at 18 hr.

The purity of the isolated Apogen P-1a, Apogen P-1b and Apogen P-1c were checked with SDS-polyacrylamide gel electrophoresis stained with silver staining.

(1) Apogen P-1a: As shown in FIG. 5, a protein band with molecular weight of 70 KD was obtained. This result suggest the nearly successful purification of Apogen p-1a which have molecular weight of 70 KD on SDSPAGE.

(2) Apogen P-1b: A single faint protein band with molecular weight of 55 KD was obtained. This result suggest the successful purification of Apogen P-1b which have molecular weight of 55 KD on SDS-PAGE.

(3) Apogen P-1c: The purification of Apogen 1c by Reverse Phase chromatography leads to the Isolation of a 70 KD protein whereas the purification of Apogen 1c by preparative electrophoresis leads to the purification of a 57 KD protein. As shown in FIG. 6(A), a major protein band with molecular weight of 70 KD was obtained by Reverse Phase chromatography. A 57 KD protein, on the other hand, was isolated by preparative electrophoresis. (FIG. 6B).

B. Isolation of Apogen P-2

The Apogen P-2 present in C3H10T1/2 conditioned medium was isolated by the following steps:

Step 1: Ammonium Sulfate Precipitation

Apogen P-2 was precipitated by 80% saturated of ammonium sulfate by adding 561 g of ammonium sulfate per liter of conditioned medium. Pellet was collected by centrifugation and the proteins were dissolved in 10 mM Tris-HCI (pH 7.4).

Step 2: Hydroxylapatite Treatment

After removal of ammonium sulfate by dialysis in 10 mM Tris-HCI (pH 7.5), the dissolved proteins were incubated with Hydroxylapatite gel (Bio-Gel HTP gel, Bio-Rad) for 1 hr. After remove HTP gel by centrifugation, the activity inducing apoptosis in LNCAP cells was found to be present in the supernatant which was then further treated with Heparin agarose gel.

Step 3: Heparin Agarose Treatment

The supernatant from step 2 was further incubated with Heparin agarose (Sigma) for 1 Hr. After remove HTP gel by centrifugation, the activity inducing apoptosis in LNCAP cells was found to be present in the supernatant.

Step 4: Reverse Phase Chromatography

Apogen P-2 presents in the supernatant of Heparin agarose in step 3 was further purified by a reverse phase chromatography. Apogen P-2 was concentrated to 1 ml. One milliliter of methanol containing 0.05% trifluoacetic acid was added. Large amount of proteins were precipitated by this treatment. Whereas, the apoptosis inducing activity (P-2) remained in supernatant. The supernatant was then applied to a reverse phase RP-4 column (Micra Scientific Inc) and developed by a linear gradient constructed by solution A ($H_2O$, 0.05% TFA) and solution B Methanol, 0.05% TFA). The linear gradient was constructed by increasing solution B from 0% to 100% in solution A within 10 min (20 milliliter elution volume and thereafter the column was eluted with 100% solution B for 5 min. The reverse phase chromatogram of Apogen P-2 is shown in FIG. 9. Fractions 12–14 have activity inducing 80% cell death in LNCAP cells at 12 hr. The purity of the isolated Apogen P-2 was checked with SDS polyacrylamide gel electrophoresis stained with silver staining. A single protein band with molecular weight of 65 Kd was obtained (FIG. 10)

C. Isolation of Apogen L

The Apogen L present in the conditioned medium was isolated by the following steps:

Step 1: DE52 Absorption

The conditioned medium was incubated with the anion exchanger, DE 52 (Diethylaminoethyl cellulose, Whatman) for 1 hr. The incubation mixture was centrifuged and DE 52 which binds Apogen L was collected and washed with 10 mM Tris-HCl (pH 7.5) containing 0.15 M NaCl. Apogen L was then eluted from DE 52 cellulose by 10 mM Tris-HCl (pH 7.5) containing 0.5 M NaCl.

Step 2: Heparin Agarose Absorption

Apogen L isolated as described in step 1 was further absorbed by Heparin agarose (Sigma) by incubating Apogen L with Heparin agarose for 1 hr. Heparin agarose was collected by centrifugation and was washed with 10 mM Tris-HCl (pH 7.5). Apogen L absorbed in Heparin agarose was then eluted by 2 M NaCl.

Step 3: Q2 HPLC Chromatography

Apogen L isolated as described above was concentrated and loaded onto a Q2 column (Bio Rad) which is further developed by a linear gradient constructed by buffer A (10 mM Tris-HCl, pH 7.4) and buffer B (10 mM 22 Tris-HCl, pH 7.4. 0.5 M NaCl) using Bio-Rad's BioLogic HPLC system. The linear gradient was constructed by increasing buffer B from 0% to 100% in buffer A in 10 min. The chromatogram is shown in FIG. 10. The purity of the isolated Apogen L was checked with SDS polyacrylamide gel electrophoresis stained with silver staining. A single protein band have activity with molecular weight of approximately 55 Kd was obtained (FIG. 11).

4. Isolation of Bovine Fetuin as Component of Protein P-2 and Apoptotic Effect Thereof in Tumor Cell Lines The observation that Apogen P-1a, P-1b, P-1c, P-2 and L were isolated from embryonic cell lines led us to speculate that new born or embryonic tissue may secrete "Apogen" that may selectively induce apoptosis in tumor cell lines. Due to this speculation, a protein named "Fetuin" has thus raised our attention based on the following reasons: (1) Fetuin is mainly a fetal protein, in the sense that the highest concentrations are found in serum and body fluids of embryos and fetuses. For example, the concentration of fetuin in bovine serum drastically decreases, probably within a few days after birth, to 1–2% of the fetal level (Yang, et al., Biochim. Biophy. Acta. 1130, 149–156 1992) (2) A histochemical study has shown that fetuin may control tissue remodelling and physiological cell death during embryonic development (Von Bulow, et al., Histochemistry 99:13–22, 1993). This result raises the possibility that fetuin may contain activity inducing cell death (apoptosis).

Additionally, a protein with an amino acid sequence identical to Fetuin was isolated from the preparation of Apogen P-2. Thus, the composition of Apogen P-2 consists at least in part of fetuin.

We therefore prepare/obtain fetuin and test in our apoptosis assay. Interestingly, we found that only bovine fetuin that is prepared by a special method is able to induce apoptosis in tumor cell lines. The commercial fetuin that is prepared by ammonium sulfate precipitation and EDTA treatment was found to contain very low activity in inducing apoptosis in tumor cells.

A. Preparation of Bovine Fetuin

Bovine fetuin was prepared by the modified Spiro method (Spiro R. G. Journal of Biological Chemistry 235, 10: 2860, 1960) according to the following steps:

1. One hundred milliliters of Fetal Bovine Serum (FBS).
2. Add two hundred milliliters of 0.05 M Zinc Acetate containing 30% (V/V) ethanol, adjust to pH 6.4 by 1M $NH_4OH$—$NH_4Cl$, let stand 15 hours at −5° C.
3. Collect the supernatant by centrifugation, add 1.0 M Barium Acetate and 95% ethanol to give 0.03 M Barium Acetate, 25% ethanol. Let stand 2 hours at −5° C.
4. Collect the supernatant by centrifugation, add 95% ethanol to give 40% ethanol. Let stand 15 hours at −10° C.
5. Collect the precipitate. Dissolve the pellet by Phosphate buffer saline.

The purified fetuin showed a single protein band with apparent molecular weight of 63 Kd on SDS-PAGE.

B. Induction of Apoptosis in Tumor Cell Lines Using Bovine Fetuin

Fetuin purified from fetal bovine serum by the procedure described above was dissolved in phosphate buffer saline (PBS). The free Zinc Acetate and Barium Acetate were removed by repetitive concentration. Fetuin was tested in LNCaP and HL-60 cells. LNCAP or HL-60 (1,000 cells) was seeded 10 microliters RPMI containing 15% or 20% Fetal bovine serum, penicillin and streptomycin at 37 degree, 5% $CO_2$ in microtray plates (25 μl wells, Robbins Scientific Corp.). Fetuin (in 10 μl PBS) at concentration of 100 ng/ml was added 3–4 hours after cells were seeded. After incubation of the tested sample with cells for 15 hours, two microliters of Hoechst dye (0.03 ng/ml in PBS) was added. Two hours later, cells that were stained with Hoechst dye were examined under fluorescence microscope. The nuclei of apoptotic cells showed DNA condensation and fragmentation can be easily identified by Hoechst dye staining. The percentage of apoptotic cells was calculated by the following equation:

% Apoptotic cells=Number of cells with DNA condensation and fragmentation/Total cell number As shown in FIG. 16(A), the nuclei of the LNCaP cells that have been incubated with control sample (PBS) are normal and healthy (A). However, the nuclei of the LNCAP cells that have been incubated with fetuin (100 ng/ml in PBS) show the characteristics of apoptosis (FIG. 16(B)). First, the cells in the presence of fetuin showed the condensation of nucleus, demonstrated by the more intense fluorescent light compared with the control nucleus in FIG. 16(A). Secondly, the nucleus condensation is accompanied by the fragmentation of DNA, demonstrated by the breakage of nucleus as shown in FIG. 16(B). As the nucleus condensation and DNA fragmentation are the two morphological characteristics of cells under apoptosis. These results suggest that fetuin contains an activity inducing apoptosis in LNCAP cells. As shown in FIG. 17(A), the nuclei of the HL-60 cells that have been incubated with control buffer (PBS) are normal and healthy(A). However, the nuclei of the HL-60 cells that have been incubated with fetuin show the characteristics of apoptosis (FIG. 17(B)). Fetuin causes the condensation of nucleus, demonstrated by the more intense fluorescent light compared with the control nucleus in FIG. 17(A). Secondly, the nucleus condensation is accompanied by the fragmentation of DNA, demonstrated by the breakage of nucleus as shown in FIG. 17(B). As we have mentioned above, the nucleus condensation and DNA fragmentation are the two morphological characteristics of cells under apoptosis. These results suggest that fetuin contains an activity inducing apoptosis in HL-60 cells.

(C) Bovine Fetuin Selectively Induces Apoptosis in Cancer Without Having Effect on Normal Cell Lines We compared the effect of fetuin on the induction of apoptosis in various cell lines. As shown in FIG. 18, at concentration 50 $\mu$g/ml, fetuin prepared as described above strongly induced apoptosis in tumor cell lines such as: LNCAP (prostate cancer), PC-3 (prostate cancer), HL-60 (leukemia), MCF-7 (breast cancer), Colo 205 (colon cancer), Calu-1 (lung cancer). Normal lung fibroblast (CCD 39 Lu) on the other hand, is not affected by fetuin.

Figure 19B:
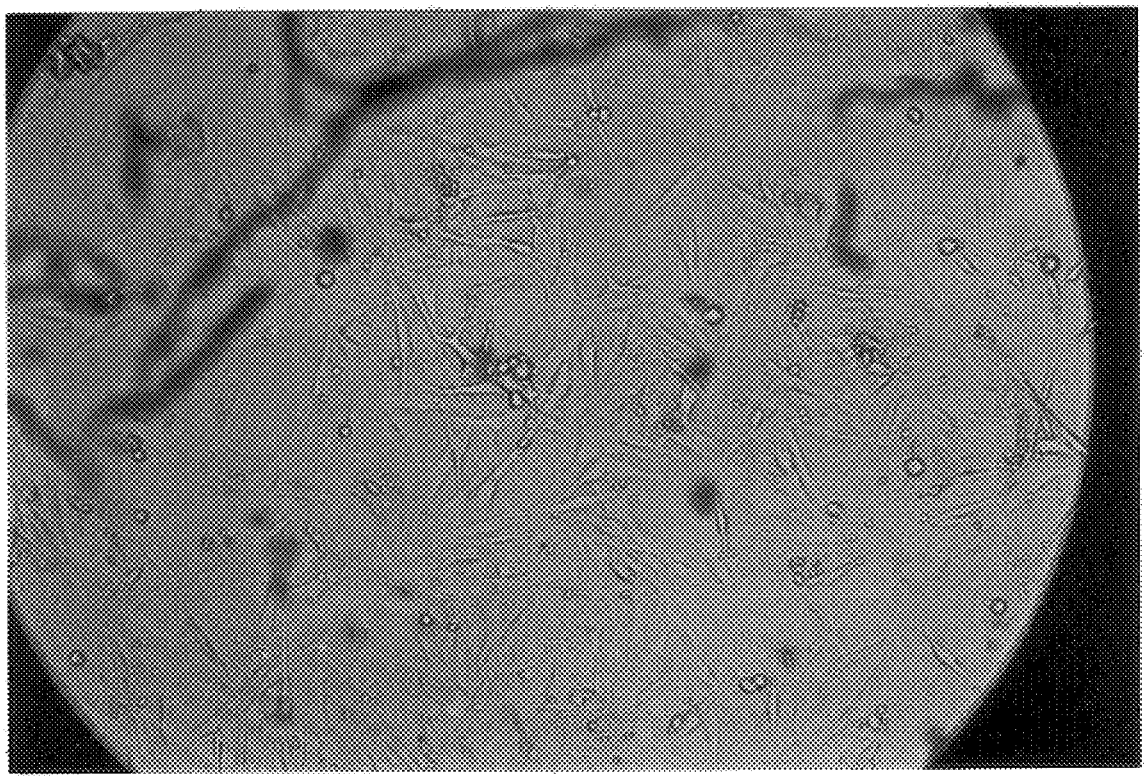
Figure 20B:
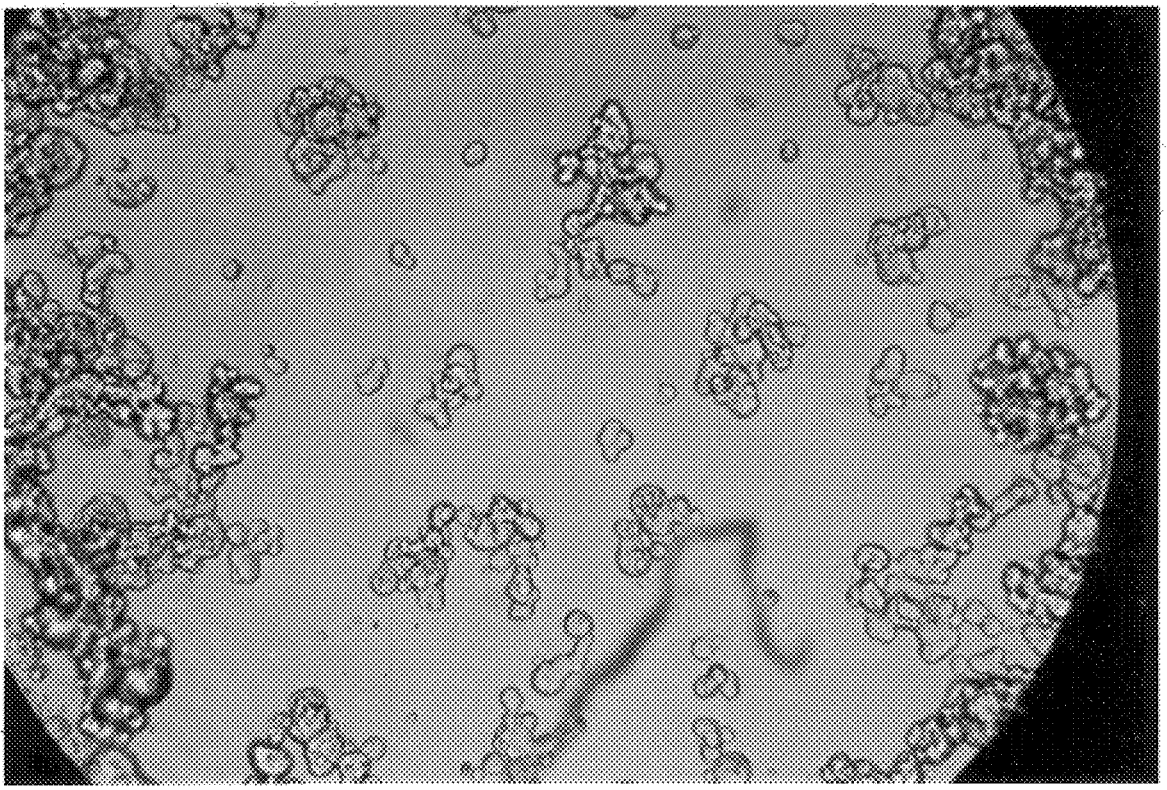

Fetuin was found to be inactive in inducing apoptosis in CCD 39 Lu cells (normal lung fibroblast) at the concentration (25 $\mu$g/ml) that highly induced apoptosis in LNCAP (prostate cancer) or HL-60 cells (leukemia). Fetuin (25 $\mu$g/ml) prepared as described above was incubated with CCD 39 Lu cells grown in MEM in microtray plate for 15 hours. As shown in FIG. 19, the CCD 39 Lu cells remained morphologically unchanged in the presence of fetuin (FIG. 19B). At this concentration (25 $\mu$g/ml) of fetuin, as shown in FIG. 20, in the presence of fetuin, less MCF-7 cell remaining, due to cell death and cell shrinkage, was observed (FIG. 20(B))

(D) Only Fetuin Prepared by the Method Described Above is Able to Induce Apoptosis in Tumor Cell Lines We found that fetuin purchased from Sigma have very low activity in inducing apoptosis in LNCAP cells. However, fetuin (25 $\mu$g/ml) prepared in our laboratory by the method described in Section 4.A above induce apoptosis in LNCaP cells by up to 90% in 4 hours. For the fetuin purchased from Sigma, apoptosis inducing activity was observed only at a very high concentration (>250 $\mu$g/ml) and at long incubation time (2 days). We estimated that the activity of fetuin prepared in our laboratory is more than fifty thousand folds higher than that of fetuin prepared by other methods.

We have examined the preparation method for Sigma's fetuin and found that these fetuins are prepared by methods including ammonium sulfate precipitation and EDTA treatment. Both treatments may cause the deprivation of Zinc ion from the protein which may cause the irreversible loss of the protein activity.

DISCUSSION

This invention describes the methods for the isolation of five proteins (Apogen P-1a, Apogen P-1b, Apogen P-1c, Apogen P-2 and Apogen L) that are able to induce apoptosis in prostate cancer cells (Apogen P-1's), in prostate cancer cells and breast cancer cells (Apogen P-2), and leukemia and breast cancer cells (Apogen L), as well as the identification of fetuin as a component of Apogen P-2. The following evidence lead us to believe that these apoptosis-inducing proteins are novel and that they have never been found before: Tumor Necrosis Factor (TNF), Transforming Growth Factor (TGF-Beta), Fas ligand and TRAIL are the proteins reported to induce apoptosis in certain cell lines. (Lin, J. K. et al., Cancer Research 52:385, 1992. Kawakawi, et al., J. of Cellular Physiology 138:1, 1989; Wiley, S. R. et al., Immunity 3:673, 1995; Krammer, et al. "Apoptosis in the APO-1 System", Apoptosis: The molecular Basis of Cell Death, Cold Spring Harbor Laboratory Press p. 87, 1991). Evidences suggested that these five proteins are different from any of these known proteins inducing apoptosis as described below:

(1) The activities are different. In our assays, TNF and TGF induced apoptosis in liver cancer cells without effects in prostate cancer (LNCAP cells) even a very high dose (100 ng/ml) are used. Whereas Apogen P-1's and Apogen P-2 induced apoptosis in prostate cancer rather than in cancer liver cells.

(2) TRAIL and Fas are membrane bound proteins, (Wiley, S. R. et al. Immunity 3:673, 1995; Krammer, et al., "Apoptosis in the APO-1 System", Apoptosis: The molecular Basis of Cell Death, Cold Spring Harbor Laboratory Press, p. 87, 1991) whereas the Apogen P-1a, Apogen P-1b, Apogen P-1c, Apogen P-2 and Apogen L are all soluble (non-membrane bound) proteins.

(3) The molecular weights of TNF, TGF and Fas ligand TRAIL are around 17–40 Kd (TNF=17 KD, TGF=24 KD, TRAIL=32 KD, Fas ligand=43 KD) (McGrath, M. H. Clinics in Plastic surgery 17:421, 1993; Wiley, S. R. et al., Immunity 3:673, 1995; Krammer, et al., "Apoptosis in the APO-1 System", Apoptosis: The molecular Basis of Cell Death, Cold Spring Harbor Laboratory Press, p. 87, 1991) whereas the molecular weight of Apogen P-1a, Apogen P-1b, Apogen P-1c, Apogen P-2 and Apogen L are between 55–70 Kd.

We claim:

1. A method of inducing apoptosis in cancer cells by administering fetuin to said cancer cells.

2. A method of inducing apoptosis in cancer cells by administering fetuin to said cancer cells, wherein said cancer cells are prostate cancer cell, leukemia cells, breast cancer cells, colon cancer cells or lung cancer cells.

* * * * *